US009102937B2

(12) United States Patent
Filichev et al.

(10) Patent No.: US 9,102,937 B2
(45) Date of Patent: Aug. 11, 2015

(54) STABLE AND SELECTIVE FORMATION OF HOOGSTEEN-TYPE TRIPLEXES AND DUPLEXES USING TWISTED INTERCALATING NUCLEIC ACIDS (TINA) AND PROCESS FOR THE PREPARATION OF TINA

(75) Inventors: Vyachelsav V. Filichev, Palmerston North (NZ); Erik Bjerregaard Pedersen, Odense (DK)

(73) Assignee: Tina Holding APS, Arhus N (DK)

( * ) Notice: Subject to any disclaimer, the term of this patent is extended or adjusted under 35 U.S.C. 154(b) by 1108 days.

(21) Appl. No.: 11/915,152

(22) PCT Filed: May 24, 2006

(86) PCT No.: PCT/DK2006/050022
§ 371 (c)(1),
(2), (4) Date: Jun. 30, 2008

(87) PCT Pub. No.: WO2006/125447
PCT Pub. Date: Nov. 30, 2006

(65) Prior Publication Data
US 2009/0216003 A1    Aug. 27, 2009

(30) Foreign Application Priority Data

May 25, 2005 (DK) .................................. 2005 00762

(51) Int. Cl.
*C12N 15/11* (2006.01)
*C07H 21/00* (2006.01)

(52) U.S. Cl.
CPC .............. *C12N 15/111* (2013.01); *C07H 21/00* (2013.01); *C12N 2310/15* (2013.01); *C12N 2310/332* (2013.01); *C12N 2310/3511* (2013.01)

(58) Field of Classification Search
None
See application file for complete search history.

(56) References Cited

U.S. PATENT DOCUMENTS

| 4,547,569 | A  | 10/1985 | Letsinger et al. |
| 5,681,940 | A  | 10/1997 | Wang et al. |
| 2002/0160972 | A1 | 10/2002 | Cook et al. |

FOREIGN PATENT DOCUMENTS

| WO | WO 96/04788 | 2/1996 |
| WO | WO 03/051901 A2 | 6/2003 |
| WO | WO 2005/083084 A1 | 9/2005 |

OTHER PUBLICATIONS

Armitage et al., Peptide nucleic acid (PNA)/DNA hybrid duplexes: intercalation by an internally linked anthraquinone, 1998, Nucleic Acids Research, vol. 26, pp. 715-720.*
Hans-Achim Wagenknecht, Synthetic oligonucleotide modifications for the investigation of charge transfer and migration processes in DNA, 2004, Current Organic Chemistry, vol. 8, pp. 251-266.*
Korshun et al., 5-(1-pyrenylethynyl)-2'-deoxyuridine, a novel fluorescent nucleoside analogue, 1996, Russian Journal of Bioorganic Chemistry, vol. 22, pp. 807-809.*
Henry et al., Efforts to expand the genetic alphabet: identification of a replicable unnatural DNA self-pair, 2004, Journal of the American Chemical Society, vol. 126, pp. 6923-6931.*
Gianolio et al., Tethered naphthalene diimide intercalators enhance DNA triplex stability, 2001, Bioorganic & Medicinal Chemistry, vol. 9, pp. 2329-2334.*
Gaugain et al., DNA bifunctional intercalators. 1. Synthesis and conformational properties of an ethidium homodimer and of an acridine ethidium heterodimer, 1978, Biochemistry, vol. 17, pp. 5071-5078.*
Keppler et al., DNA triple helix stabilisation by a naphthylquinoline dimer, 1999, FEBS Letters, vol. 447, pp. 223-226.*
John O. Trent, "[14] Molecular Modeling of Drug—DNA Complexes: An Update", Methods in Enzymology, vol. 340, 2001, pp. 290-326.
Taco G. Uil et al., "Therapeutic modulation of endogenous gene function by agents with designed DNA-sequence specificities", Nucleic Acids Research, 2003, vol. 31, No. 21, pp. 6064-6078.
Melissa P. Knauert et al., "Triplex forming oligonucleotides: sequence-specific tools for gene targeting", Human Molecular Genetics, 2001, vol. 10, No. 20, 2243-2251.
Ramareddy V. Guntaka et al., "Triplex-forming oligonucletides as modulators of gene expression", The International Journal of Biochemistry & Cell Biology, 35, (2003) 22-31.
Sabrina Buchini et al., "Stable and Selective Recognition of Three Base Pairs in the Parallel Triple Helical DNA Binding Motif", Angew. Chem. 2004, 116, 4015-4018.
Marcella Faria et al., "Triplex-forming molecules: from concepts to applications", The Journal of Gene Medicine, J. Gene Med. 2001, 3: 299-310.
Darren M. Gowers et al., "Towards mixed sequence recognition by triple helix formation", Nucleic Acids Research, 1999, vol. 27, No. 7, pp. 1569-1577.
Peter E. Nielsen et al., "Sequence-Selective Recognition of DNA by Strand Displacement with a Thymine-Substituted Polyamide", Science, vol. 254, Dec. 6, 1991, pp. 1497-1500.
H. Jakob Larsen et al., "Antisense properties of peptide nucleic acid", Biochimica et Biophysica Acta 1489 (1999) 159-166.

(Continued)

*Primary Examiner* — Dana Shin
(74) *Attorney, Agent, or Firm* — Foley & Lardner LLP

(57) ABSTRACT

The present invention describes a flexible basestacking monomer that can be incorporated into an oligonucleotide or oligonucleotide analogue, as well as triplex forming oligonucleotides comprising the flexible basestacking monomer. Triplex forming oligonucleotides of the invention are capable of binding sequence specifically to doublestranded target nucleic acids and are therefore of interest for modulation of the activity of target nucleic acids and also detection of target nucleic acids.

2 Claims, 6 Drawing Sheets

(56) References Cited

OTHER PUBLICATIONS

Vadim V. Demidov et al., "Sequence-Specific Targeting of Duplex DNA by Peptide Nucleic Acids via Triplex Strand Invasion", Methods 23, 108-122 (2001).
Satoshi Obika et al., "Triplex-forming enhancement with high sequence selectivity by single 2'-O,4'-C-methylene bridged nucleic acid (2',4'-BNA) modification", Tetrahedron Letters 41 (2000) 8923-8927.
Bei-Wen Sun et al., "Sequence and pH Effects of LNA-Containing Triple Helix-Forming Oligonucleotides: Physical Chemistry, Biochemistry and Modeling Studies", Biochemistry 2004, 43, 4160-4169.
Marcel J. J. Blommers et al., "Dual Recognition of Double-Stranded DNA by 2'-Aminoethoxy-Modified Oligonucleotides: The Solution Structure of an Intramolecular Triplex Obtained by NMR Spectroscopy", Biochemistry 1998, 37, 17714-17725.
Bernard Cuenoud et al., "Zweifache Erkennung von Doppelstrangiger DNA durch 2'-Aminoethoxy-modifizierte Oligonucleotide", Angew. Chem. 1998, 110, Nr. 9, pp. 1350-1353.
Bernard Cuenoud et al., "Dual Recognition of Double-Stranded DNA by 2'-Aminoethoxy-Modified Oligonucleotides", Angew. Chem. Int. Ed. 1998, 37, No. 9, pp. 1288-1291.
Sergei M. Grayaznov et al., "Oligonucletide N3" → P5' Phosphoramidates", Proc. Natl. Acad. Sci. USA, vol. 92, pp. 5798-5802, Jun. 1995.
Christophe Escude et al., "Stable triple helices formed by oligonucletide N3' →P5' phosphoramidates inhibit transcription elongation", Proc. Natl. Acad. Sci. USA vol. 93, pp. 4365 4369, Apr. 1996.
Christophe Marchand et al., "Stabilization of Triple Helical DNA by a Benzopyridoquinoxaline Intercalator", Biochemistry 1996, 35, 5022-5032.
Shrikant Kukreti et al., "Triple helices formed at oligopyrimidine-oligopurine sequences with base pair inversions: effect of a triplex-specific ligand on stability and selectivity", Nucleic Acids Research, 1998, vol. 26, No. 9, pp. 2179-2183.
Sarah A. Cassidy et al., "DNA sequence specificity of a naphthylquinoline triple helix-binding ligand", Nucleic Acids Research, 1996, vol. 24, No. 21, 4133-4138.
Christophe Escude et al., "Ligand-Induced Formation of Triple Helices with Antiparallel Third Strands Containing G and T", Biochemistry, 1996, 35, 5735-5740.
Lucjan Strekowski et al., "Bis-4-aminoquinolines: Novel Triple-Helix DNA Intercalators and Antagonists of Immunostimulatory CpG-Oligodeoxynucleotides", Bioorganic and Medicinal Chemistry 11 (2003) 1079-1085.
Lucjan Strekowski et al., "New Triple-helix DNA stabilizing agents", Bioorganic and Medicinal Chemistry Letters 15, (2005) 1097-1100.
Karin Sandstrom et al., "The influence of intercalator binding on DNA triplex stability: correlation with effects on A-tract duplex structure", Journal of Molecular Recognition, J. Mol. Recognit. 2004, 17: 277-285.
Nitin Puri et al., "Synthesis of 5'-Polyarene-Tethered Oligo-DNAs and the Thermal Stability and Spectroscopic Properties of Their Duplexes and Triplexes", Tetrahedron, vol. 53, No. 30, pp. 10409-10432, 1997.
Jean-Francois Mouscadet et al., "Triple Helix Formation with Short Oligonucleotide-Intercalator Conjugates Matching the HIV-1 U3 LTR End Sequence", Biochemistry 1994, 33, 4187-4196.
S. Mohammadi et al., "Triple Helix Formation and Homologous Strand Exchange in Pyrene-Labeled Oligonucleotides", Biochemistry, 1997, 36, 14836-14844.
Ulysse Asseline et al., "Synthesis and binding properties of perylene-oligo-2'-deoxyribonucleotide conjugates", Tetrahedron Letters 42 (2001) 9005-9010.
Bei-wen Zhou et al., "Stable Triple Helices Formed by Acridine-Containing Oligonucleotides with Oligopurine Tracts of DNA Interrupted by One or Two Pyrimidines", J. Am. Chem. Soc. 1995, 117, 10425-10428.

Shrikant Kukreti et al., "Extension of the range of DNA sequences available for triple helix formation: stabilization of mismatched triplexes by acridine containing oligonucleotides", Nucleic Acids Research, 1997, vol. 25, No. 21, pp. 4264-4270.
Dimitri Ossipov et al., "Dipyrido[3,2-α:2',3'-c] phenazine-Tethered Oligo-DNA: Synthesis and Thermal Stability of Their DNA-DNA and DNA-RNA Duplexes and DNA-DNA-DNA Triplexes", Helvetica Chimica Acta—vol. 82, 1999, pp. 2186-2200.
Adel A.-H. Abdel-Rahman et al., "Insertion of 5-Methyl-N4-(1-pyrenylmethyl) cytidine into DNA Duplex, Three-way Junction and Triplex Stabilities", Tetrahedron, vol. 52, No. 48, pp. 15311-15324, 1996.
Yves Aubert et al., "Synthesis and Hybridization properties of oligonucleotide-perylene conjugates: influence of the conjugation parameters on triplex and duplex stabilities", Org. Biomol. Chem. 2004, 2, 3496-3503.
Ulf B. Christensen et al., "Intercalating nucleic acids containing insertions of 1-O-(1-pyrenylmethyl)glycerol: stabilization of dsDNA and discrimination of DNA over RNA", Nucleic Acids Research, 2002, vol. 30, No. 22, pp. 4918-4925.
Ulf B. Christensen et al., "Intercalating Nucleic Acids and Pyrene Nucleotide Analogues as Next-Nearest Neighbors for Excimer Fluorescence Detection of Single-Point Mutation Under Nonstringent Hybridization Conditions", Helvetica Chimica Acta—vol. 86 (2003), pp. 2090-2097.
Vyacheslav V. Filichev et al., "Intercalating nucleic acids (INAs) with insertion of N-(pyren-1-ylmethyl)-(3R,4R)-4-(hydroxymethyl)pyrrolidin-3-ol. DNA (RNA) duplex and DNA three-way junction stabilities", Org. Biomol. Chem. 2003, 1, 100-103.
Vyacheslav V. Filichev et al., "Intercalating nucleic acids: the inversion of the stereocentre in 1-O-(pyren-1-ylmethyl)glycerol from R to S. Thermal stability towards ssDNA, ssRNA and its own type of oligodeoxynucleotides", Tetrahedron Letters, 45, (2004) 4907-4910.
Ulf B. Christensen et al., "Intercalating Nucleic Acids: The Influence of Linker Length and Intercalator Type on Their Duplex Stabilities", Nucleosides, Nucleotides and Nucleic Acids, vol. 23, No. 1 & 2, pp. 207-225, 2004.
Christina B. Nielsen et al., "NMR Structure Determination of a Modified DNA Oligonucleotide Containing a New Intercalating Nucleic Acid", Bioconjugate Chem. 2004, 15, 260-269.
Vyacheslav V. Filichev et al., "Enhanced Inhibition of Transcription Start by Targeting with 2'-OMe Pentaribonucleotides Comprising Locked Nucleic Acids and Intercalating Nucleic Acids", ChemBioChem 2005, 6, 1181-1184.
Vyacheslav V. Filichev et al., "Locked Nucleic Acids and Intercalating Nucleic Acids in the Design of Easily Denaturing Nucleic Acids: Thermal Stability Studies", ChemBioChem 2004, 5, 1673-1679.
Sabine Louet, "Human Genetic Signatures", Bioentrepreneur Jun. 213, 2003: http://dx.doi.org/10.1038/bioent748.INA®.
Shoeb L. Khan et al., "Palladium(0)-Catalyzed Modification of Oligonucleotides during Automated Solid-Phase Synthesis", J. Am. Chem. Soc. 1999, 121, 4704-4705.
Amy E. Beilstein et al., "On-column derivatization of oligodeoxynucleotides with ferrocene", Chem. Commun. 2000, 509-510.
Manuela Rist et al., "Preparation of 1-Ethynylpyrene-Modified DNA via Sonogashira-Type Solid-Phase Couplings and Characterization of the Fluorescence Properties for Electron Transfer Studies", Eur. J. Chem. 2003, 2498-2504.
Elke Mayer et al., "1-Ethynylpyrene as a Tunable and Versatile Moleuclar Beacon for DNA", ChemBioChem 2004, 5, 865-868.
Zev J. Gartner et al., "Expanding the Reaction Scope of DNA-Templated Synthesis", Angew. Chem. 2002, 114, Nr 10, 1874-1878.
Zev J. Gartner et al., "Expanding the Reaction Scope of DNA-Templated Synthesis", Angew. Chem. Int. Ed., 2002, 41, No. 10, 1796-1800.
Zev. J. Gartner et al., "Two Enabling Architectures for DNA-Templated Organic Synthesis", Angew. Che. 2003, 115, Nr. 12, 1408-1413.
Zev J. Gartner et al., "Two Enabling Architectures for DNA Templated Organic Synthesis", Angew. Che. Ind. eD. 2003, 42, No. 12, pp. 1370-1375.

(56) References Cited

OTHER PUBLICATIONS

Bo Liang et al., "Copper-Free Sonogashira Coupling Reaction with PdCl2 in Water under Aerobic Conditions", J. Org. Chem, 2005, 70, 391-393.
Gary Felsenfeld et al., "The Physical and Chemical Properties of Nucleic Acids", Annu. Rev. Biochem. 1967:36:407-448.
Keliang Liu et al., "A Novel DNA Duplex. A Parallel-Stranded DNA Helix with Hoogsteen Base Pairing", Biochemistry 1993, 32, 11802-11809.
Rex X.-F. Ren et al., "Naphthalene, Phenanthrene, and Pyrene as DNA Base Analogues: Synthesis, Structure, and Fluorescence in DNA", J. Am. Chem. Soc. 1996, 118, 7671-7678.
Kevin M. Guckian et al., "Experimental Measurement of Aromatic Stacking Affinities in the Context of Duplex DNA", J. Am. Chem. Soc. 1996, 118, 8182-8183.
Stefan Hildbrand et al., "5-Substituted 2-Aminopyridine C-Nucleosides as Protonated Cytidine Equivalents: Increasing Efficiency and Selectivity in DNA Triple-Helix Formation", J. Am. Chem. Soc. 1997, 119, 5499-5511.
Andrei D. Malakhov et al., "1-(Phenylethynyl)pyrene and 9,10-Bis(phenylethynyl)anthracene, Useful Fluorescent Dyes for DNA Labeling: Excimer Formation and Energy Transfer", Eur. J. Org. Chem. 2004, 1298-1307.
Michael Hausmann et al., "COMBO-FISH: specific labeling of nondenatured chromatin targets by computer-selected DNA oligonucleotide probe combinations", BioTechniques vol. 35, No. 3 (2003) pp. 564-577.
P. Wils et al., "Efficient purification of plasmid DNA for gene transfer using triple-helix affinity chromatography", Gene Therapy (1997) 4, 323-330.
Thomas Schluep et al., "Purification of plasmids by triplex affinity interaction", Nucleic Acids Research, 1998, vol. 26, No. 19, 4524-4528.
Matteo D. Costioli et al., "DNA Purification by Triple-Helix Affinity Precipitation", Biotechnology and Bioengineering, vol. 81, No. 5, Mar. 5, 2003, pp. 535-545.
Chin-Yi Huang et al., "Triplex Formation by an Oligonucleotide Containing N4-(3-Acetamidopropyl)cytosine", J. Org. Chem. 1993, 58, 5048-5049.
Isabelle Prevot-Halter et al., "Selective Recognition of a C-G Base-Pair in the Parallel DNA Triple-Helical Binding Motif", Bioorganic & Medicinal Chemistry Letters 9 (1999)2657-2660.
Satoshi Obika et al., "Stable Oligonucleotide-Directed Triplex Formation at Target Sites with CG Interruptions: Strong Sequence-Specific Recognition by 2', 4'-Bridged Nucleic-Acid-Containing 2-Pyridones under Physiological Conditions", Chem. Eur. J. 2002, 8, No. 20, 4796-4802.
Sabrina Buchini et al., "Stable and Selective Recognition of Three Base Pairs in the Parallel Triple-Helical DNA Binding Motif", Angew. Chem. Int. Ed. 2004, 43, 3925-3928.
Dominique Guianvarc'h et al., "Incorporation of a novel nucleobase allow stable oligonucleotide-directed triple helix formation at the target sequence containing a purine pyrimidine interruption", Chem. Commun. 2001, 1814-1815.
Dominique Guianvarc'h et al., "Design of Artificial Nucleobases for the Recognition of the AT Inversion of Triple-Helix Forming Oligonucleotides: A Structure-Stability Relationship Study and Neighbour Bases Effect", Bioorganic & Medicinal Chemistry, 11 (2003) 2751-2759.
Akira Ono et al., "DNA Triplex Formation of Oligonucleotide Analogues Consisting of Linker Groups and Octamer Segments That Have Opposite Sugar-Phosphate Backbone Polarities", Biochemistry 1991, 30, 9914-9921.
Brian C. Froehler et al., "Triple-Helix Formation and Cooperative Binding by Oligodeoxynucleotides with a 3'-3' Internucleotide Junction", Biochemisty 1992, 31, 1603-1609.
Therese De Bizemont et al., "Alternate strand recognition of double-helical DNA by (T,G)-containing oligonucleotides in the presence of a triple helix-specific ligand", Nucleic Acids Research, 1996, vol. 24, No. 6, pp. 1136-1143.
Therese De Bizemont et al., "New junction models for alternate-strand triple-helix formation", Chemistry and Biology Dec. 1998, 5:755-762.
Yoshihito Ueno et al., "Nucleosides and Nucleotides. 208. Alternate-Strand Triple-Helix Formation by the 3'-3'-Linked Oligodeoxynucleotides with the Anthraquinonyl Group at the Junction Point", Bioconjugate Chem. 2001, 12, 635-642.
Carsten H. Jessen et al., "Desing of an Intercalating Linker Leading to the First Efficiently 5',5'-Linked Alternate-Strand Hoogsteen Triplex with High Stability and Specificity", Helvetica Chimica Acta—vol. 87 (2004) 2465-2471.
Jesper Wengel, "Nucleic acid nanotechnology—towards Angstrom-scale engineering", Org. Biomol. Chem. 2004, 2, 277-280.
Bruno Samori et al., "DNA-Codes fur die Nanowissenschaften", Angew. Chem. Int. Ed. 2005, 117, 1190-1206.
Bruno Samori et al., "DNA Codes for Nanoscience", Angew. Chem. Int. Ed. 2005, 44, 1166-1181.
Vyacheslav V. Filichev et al., "Stable and Selective Formation of Hoogsteen-Type Triplexes and Duplexes Using Twisted Intercalating Nucleic Acids (TINA) Prepared via Postsynthetic Sonogashira Solid-Phase Coupling Reactions", J. Am. Chem. Soc., 2005, 127, 14849-14858.
Takanori Miyashita et al., "Novel dinucleoside phosphotriester unit conjugated with an intercalative moiety in a stereospecific manner enhances thermal stability of an alternate-stranded triple helix", Tetrahedron Letters 44, (2003) 7399-7402.
Imrich Geci et al., "Synthesis of Twisted Intercalating Nucleic Acids Possessing Acridine Derivatives. Thermal Stability Studies", Bioconjugate Chem. 2006, 17, 950-957.
Arturo Anguiano, "Fluorescence In Situ Hybridization (FISH): Overview and Medical Applications", Journal of Clinical Ligand Assay, vol. 23, No. 1, Spring 2000, pp. 33-42.
Sabrina Buchini et al., "Recent improvements in antigene technology", Current Opinion in Chemical Biology 2003, 7:717-726.

* cited by examiner

```
                        SEQUENCE LISTING

<160> NUMBER OF SEQ ID NOS: 32

<210> SEQ ID NO 1
<211> LENGTH: 14
<212> TYPE: DNA
<213> ORGANISM: Artificial
<220> FEATURE:
<223> OTHER INFORMATION: Synthetic oligonucleotide

<400> SEQUENCE: 1
cccctttctt tttt                                                        14

<210> SEQ ID NO 2
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 1

<400> SEQUENCE: 2 cccctttntct ttttt                                                       15

<210> SEQ ID NO 3
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 2

<400> SEQUENCE: 3 cccctntct ttttt                                                         15

<210> SEQ ID NO 4
<211> LENGTH: 15
```

-continued

```
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 3

<400> SEQUENCE: 4
ccccttntct ttttt                                                   15

<210> SEQ ID NO 5
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 4

<400> SEQUENCE: 5
ccccttntct ttttt                                                   15

<210> SEQ ID NO 6
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 5

<400> SEQUENCE: 6
ccccttntct ttttt                                                   15

<210> SEQ ID NO 7
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: Intercalator 5

<400> SEQUENCE: 7 ccccttcnt ttttt                                                    15

<210> SEQ ID NO 8
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: Intercalator 5

<400> SEQUENCE: 8 ccccttnct ttttt                                                    15

<210> SEQ ID NO 9
```

```
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: Intercalator 5

<400> SEQUENCE: 9
cccnctttct ttttt                                                    15

<210> SEQ ID NO 10
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Intercalator 5

<400> SEQUENCE: 10 nccctttct ttttt                                                     15

<210> SEQ ID NO 11
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Intercalator 5
<220> FEATURE:
<221> NAME/KEY: misc_feature
<222> LOCATION: (8)..(8)
<223> OTHER INFORMATION: Intercalator 5

<400> SEQUENCE: 11
nccccttntc tttttt                                                   16

<210> SEQ ID NO 12
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 5
<220> FEATURE:
<221> NAME/KEY: misc_feature
<222> LOCATION: (9)..(9)
<223> OTHER INFORMATION: Intercalator 5

<400> SEQUENCE: 12
ccccttntnc tttttt                                                   16

<210> SEQ ID NO 13
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
```

-continued

```
<222> LOCATION: (6)..(6)
<223> OTHER INFORMATION: Intercalator 5
<220> FEATURE:
<221> NAME/KEY: misc_feature
<222> LOCATION: (9)..(9)
<223> OTHER INFORMATION: Intercalator 5

<400> SEQUENCE: 13
cccctnttnc tttttt                                                       16

<210> SEQ ID NO 14
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 5
<220> FEATURE:
<221> NAME/KEY: misc_feature
<222> LOCATION: (11)..(11)
<223> OTHER INFORMATION: Intercalator 5

<400> SEQUENCE: 14 cccttntct nttttt                                                        16

<210> SEQ ID NO 15
<211> LENGTH: 17
<212> TYPE: DNA
<213> ORGANISM: Artificial
<220> FEATURE:
<223> OTHER INFORMATION: Synthetic oligonucleotide

<400> SEQUENCE: 15
gacggggaaa gaaaaaa                                                      17

<210> SEQ ID NO 16
<211> LENGTH: 14
<212> TYPE: DNA
<213> ORGANISM: Artificial
<220> FEATURE:
<223> OTHER INFORMATION: Synthetic oligonucleotide

<400> SEQUENCE: 16
ggggaaagaa aaaa                                                         14

<210> SEQ ID NO 17
<211> LENGTH: 17
<212> TYPE: DNA
<213> ORGANISM: Artificial
<220> FEATURE:
<223> OTHER INFORMATION: Synthetic oligonucleotide

<400> SEQUENCE: 17
gacggggaat gaaaaaa                                                      17

<210> SEQ ID NO 18
<211> LENGTH: 17
<212> TYPE: DNA
<213> ORGANISM: Artificial
<220> FEATURE:
<223> OTHER INFORMATION: Synthetic oligonucleotide

<400> SEQUENCE: 18
gacggggaag gaaaaaa                                                      17
```

```
<210> SEQ ID NO 19
<211> LENGTH: 17
<212> TYPE: DNA
<213> ORGANISM: Artificial
<220> FEATURE:
<223> OTHER INFORMATION: Synthetic oligonucleotide

<400> SEQUENCE: 19
gacggggaac gaaaaaa                                                   17

<210> SEQ ID NO 20
<211> LENGTH: 18
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: Intercalator 5

<400> SEQUENCE: 20 tttttctnt tccccgtc                                                   18

<210> SEQ ID NO 21
<211> LENGTH: 18
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Intercalator 5

<400> SEQUENCE: 21
gacggggaan agaaaaaa                                                  18

<210> SEQ ID NO 22
<211> LENGTH: 12
<212> TYPE: DNA
<213> ORGANISM: Artificial
<220> FEATURE:
<223> OTHER INFORMATION: Synthetic oligonucleotide

<400> SEQUENCE: 22
ctcaagcaag ct                                                        12

<210> SEQ ID NO 23
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 5

<400> SEQUENCE: 23
ctcaagncaa gct                                                       13

<210> SEQ ID NO 24
<211> LENGTH: 14
<212> TYPE: DNA
<213> ORGANISM: Artificial
<220> FEATURE:
<223> OTHER INFORMATION: Synthetic oligonucleotide
```

```
<220> FEATURE:
<221> NAME/KEY: misc_feature
<222> LOCATION: (6)..(6)
<223> OTHER INFORMATION: Intercalator 5
<220> FEATURE:
<221> NAME/KEY: misc_feature
<222> LOCATION: (8)..(8)
<223> OTHER INFORMATION: Intercalator 5

<400> SEQUENCE: 24
ctcaangnca agct                                                   14

<210> SEQ ID NO 25
<211> LENGTH: 12
<212> TYPE: DNA
<213> ORGANISM: Artificial
<220> FEATURE:
<223> OTHER INFORMATION: Synthetic oligonucleotide

<400> SEQUENCE: 25
agcttgcttg ag                                                     12

<210> SEQ ID NO 26
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: Intercalator 5

<400> SEQUENCE: 26
agcttgnctt gag                                                    13

<210> SEQ ID NO 27
<211> LENGTH: 12
<212> TYPE: RNA
<213> ORGANISM: Artificial
<220> FEATURE:
<223> OTHER INFORMATION: Synthetic oligonucleotide

<400> SEQUENCE: 27
agcuugcuug ag                                                     12

<210> SEQ ID NO 28
<211> LENGTH: 17
<212> TYPE: DNA
<213> ORGANISM: Artificial
<220> FEATURE:
<223> OTHER INFORMATION: Synthetic oligonucleotide

<400> SEQUENCE: 28 gacgggaaa gaaaaaa                                                 17

<210> SEQ ID NO 29
<211> LENGTH: 17
<212> TYPE: DNA
<213> ORGANISM: Artificial
<220> FEATURE:
<223> OTHER INFORMATION: Synthetic oligonucleotide

<400> SEQUENCE: 29 tttttttcttt ccccgtc                                               17

<210> SEQ ID NO 30
```

-continued

```
<211> LENGTH: 17
<212> TYPE: DNA
<213> ORGANISM: Artificial
<220> FEATURE:
<223> OTHER INFORMATION: Synthetic oligonucleotide

<400> SEQUENCE: 30 tttttcatt ccccgtc                                                    17

<210> SEQ ID NO 31
<211> LENGTH: 17
<212> TYPE: DNA
<213> ORGANISM: Artificial
<220> FEATURE:
<223> OTHER INFORMATION: Synthetic oligonucleotide

<400> SEQUENCE: 31 tttttcctt ccccgtc                                                    17

<210> SEQ ID NO 32
<211> LENGTH: 17
<212> TYPE: DNA
<213> ORGANISM: Artificial
<220> FEATURE:
<223> OTHER INFORMATION: Synthetic oligonucleotide

<400> SEQUENCE: 32 tttttcgtt ccccgtc                                                    17
```

STABLE AND SELECTIVE FORMATION OF HOOGSTEEN-TYPE TRIPLEXES AND DUPLEXES USING TWISTED INTERCALATING NUCLEIC ACIDS (TINA) AND PROCESS FOR THE PREPARATION OF TINA

CROSS REFERENCE TO RELATED APPLICATION

This application claims the benefit and priority to and is a U.S. National Phase of PCT International Application Number PCT/DK2006/050022, filed on May 24, 2006, designating the United States of America and published in the English language, which claims priority under 35 U.S.C. §119 to Danish Application Number PA 2005 00762, filed on May 25, 2005. The disclosures of the above-referenced applications are hereby expressly incorporated by reference in their entireties.

SUMMARY OF THE INVENTION

The invention relates to the field of oligonucleotides and modified oligonucleotides with improved properties, such as capability of forming triplex strands and suitability for detection, diagnosis and/or treatment.

In particular, the present invention provides novel flexible basestacking monomer which can be incorporated into an oligonucleotide providing triplex forming oligonucleotides (TFOs) capable of binding sequence specifically with target double stranded or single stranded nucleic acids to form triple helices of very high thermal stability. Other aspects are methods for synthesizing the TFOs as well as their use in detection, diagnosis and treatment.

BACKGROUND OF THE INVENTION

WO2005083084 described intercalator pseudonucleotides capable of being incorporated into the backbone of an oligonucleotide or an oligonucleotide analogue. Oligonucleotides comprising the intercalator pseudonucleotides have a reduced capability of triplex formation, but have the ability to discriminate between DNA and RNA, i.e. they form more stable complexes with DNA than with RNA.

Malakhov et al, 2004 (*Eur. J. Org. Chem.* 2004, 1298-1307) disclosed a monomer for incorporation into an oligonucleotide or an oligonucleotide. The aim of the study was to provide a natural base, i.e. a promiscuous base that can fit into a Watson-Crick helix opposite to any of the naturally occurring bases. No studies on triplex formation were reported.

The sequence-specific recognition of double-stranded DNA (dsDNA) is a topic of considerable interest in the development of oligonucleotide-based tools in molecular biology, therapeutics and bionanotechnology. Triple helices are formed when a single-stranded triplex-forming oligonucleotide (TFO) binds to dsDNA through specific major groove interactions and this has been the subject of intense research for gene targeting. This approach allows transcriptional control, gene knock-out and sequence-selective treatment of genomic DNA aiming mutated or recombined genes.

The third strand affinity of TFOs to their targets is generally problematic due to their required recognition to homopurine sequences of dsDNA and the disfavored formation of pH sensitive $C^+ \cdot G$-C Hoogsteen base triples at physiological conditions in the parallel (pyrimidine) binding motif. During the past decade, many efforts have been devoted to modify TFOs to improve binding affinity to their targets along with the design of triplex nucleobases which could alleviate restriction of the dsDNA sequence. Oligonucleotides possessing modified nucleic acids such as peptide nucleic acids (PNA), locked nucleic acids (LNA), 2'-aminoethyl-oligoribonucleotides (2'-AE-RNA) and N3'->P5' phosphoramidates inducing increased binding affinity are among the most successful chemically modified TFOs. The stabilization of the triplex structures has been also observed upon addition of heterocyclic compounds (intercalators) sometimes possessing a positively charged side chain to the aqueous solution containing all three oligonucleotide sequences. It has been also shown that an intercalator covalently linked to the 3'- or the 5'-end of a TFO led to thermal stabilization of parallel triplexes in a range of +3.0-+16.1° C. depending on linker length and type of intercalator. However, there has been limited attention to the covalently attached intercalators inserted as a bulge in the middle of TFO.

This design could have several advantages. Firstly, the synthesis of only one phosphoramidite of intercalating pseudo-nucleotides is required compared to the synthesis of at least four nucleotide monomers needed for sugar modified nucleic acids. Secondly, several bulged insertions of an intercalator monomer into the sequence could considerably increase duplex and triplex stabilities compared to the single insertion. Moreover, the structural difference between Watson-Crick and Hoogsteen binding modes along with the absence or presence of 2'-OH in DNA and RNA give rise to different properties for the various types of helixes. Therefore, bulged insertions of a linker and breaking up the helix by intercalators are expected to result in unique properties for appropriately chosen helixes. This has led to chemically modified oligonucleotides which could discriminate between different types of single-stranded nucleic acids.

DETAILED DESCRIPTION OF THE INVENTION

Bulge insertions of (R)-1-O-[4-(1-pyrenylethynyl)phenylmethyl]glycerol into the middle of homopyrimidine oligodeoxynucleotides (twisted intercalating nucleic acids, TINA) obtained via post-synthetic Sonogashira coupling reaction lead to extraordinary high thermal stability of Hoogsteen-type triplexes and duplexes, whereas Watson-Crick type duplexes of the same nucleotide content are destabilized.

In a first aspect, the present invention provides a flexible basestacking monomer with the general structure:

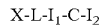

wherein X is a backbone monomer unit that can be incorporated into the backbone of a oligonucleotide or a oligonucleotide analogue, or PNA, or PNA analogues, L is a linker, $I_1$ is a first intercalator comprising at least one essentially flat conjugated system, which is capable of co-stacking with nucleobases of DNA, RNA or analogues thereof, C is a conjugator and $I_2$ is a second intercalator comprising at least one essentially flat conjugated system, which is capable of co-stacking with nucleobases of DNA, RNA or analogues thereof.

A flexible basestacking monomer consists of at least two intercalating systems $I_1$ and $I_2$ which are linked by a conjugator C which provides the necessary structural rigidity and twisting flexibility. The latter is believed to be important to help intercalators to adjust themselves to an appropriate position inside the nucleic acid helix.

In a preferred embodiment, the backbone X is capable of being incorporated into a oligonucleotide of DNA, RNA, HNA, MNA, ANA, LNA, CAN, INA, CeNA, TNA, (2'-NH)-TNA, (3'-NH)-TNA, α-L-Ribo-LNA, α-L-Xylo-LNA, β-D-

Ribo-LNA, β-D-Xylo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, 2'-OR-RNA, 2'-AE-RNA, α-L-RNA, β-D-RNA, and combinations and modifications thereof.

Nucleic acids and their analogues are providing an oligonucleotide which is able to bind to complementary nucleic acids via Watson-Crick or Hoogsteen or reverse Hoogsteen base-pairing. X can be incorporated at the 3'-end and/or at the 5'-end and/or in the middle of the sequences. Modified nucleobases, carbohydrates, peptide chains, magnetic beads, agarose beads, sepharose beads, glass, plastic surfaces, heavy metals and chip surfaces are considered as used as additional modifications of nucleic acids.

In another embodiment, the backbone monomer unit X comprises alkylendiol, such as ethylenglycol or 1-O-methyleneglycerol which optionally has the alkylenediol partly comprised in a ring system, such as glycon. For example, the backbone monomer X may be a part of four, five or six member rings which eventually have heteroatoms selected from nitrogen, sulphur, phosphorous, and oxygen.

In one embodiment, the linker L of the flexible basestacking monomer comprises 0-60 atoms.

In another embodiment, L comprises a chain or a ring or combinations thereof and/or substitutions thereof.

In still another embodiment, L comprises an alkyl chain or an oxaalkyl chain or an azaalkyl chain or a thiaalkyl chain or an carboxamide group or an thiocarboxamide group or an sulphonamide group or combinations thereof.

The combination of X and L provides a system which places intercalating system of $I_1$-C-$I_2$ in the core of nucleic acid helixes with ability to stack with nucleic acid bases.

$I_1$ of the flexible basestacking monomer of the invention is a first intercalator comprising at least one essentially flat conjugated system, which is capable of co-stacking with nucleobases of DNA, RNA or analogues thereof.

In a preferred embodiment, $I_1$ is a monocyclic or polycyclic aromatic ringsystem optionally selected from the group of a benzene, naphthalene, azulene, bicyclic heteroaromatic ring systems and substitutions thereof.

C of the flexible basestacking monomer of the invention is a conjugator. In a preferred embodiment, C is selected from the group of an alkyl of from 1 to 12 carbons, alkenyl of from 2 to 12 carbons, alkynyl 2 to 25 carbons or diazo or combinations thereof with a length of no more than 25 carbons or/and nitrogen atoms.

In another embodiment, C is selected from the group consisting of straight-chain or branched-chain or monocyclic aromatic rings and substitutions thereof which eventually have heteroatoms selected from nitrogen, sulphur, phosphorous, and oxygen. In still another embodiment, the alkenyl of C is an acetylene or repetitive acetylenes. In a preferred embodiment, the unit length of the backbone monomer unit X including a phosphorous atom is less than 6 atoms, wherein the backbone unit length is the shortest distance from one monomer to the next.

In a preferred embodiment, the linking moiety L has a length of at least 2 atoms and eventually possesses heteroatoms selected from nitrogen, sulphur, phosphorous, and oxygen.

$I_2$ of the flexible basestacking monomer is a second intercalator comprising at least one essentially flat conjugated system, which is capable of co-stacking with nucleobases of DNA, RNA or analogues thereof.

In a preferred embodiment, $I_2$ is selected from the group of bi-cyclic aromatic ringsystems, tricyclic aromatic ringsystems, tetracyclic aromatic ringsystems, pentacyclic aromatic ringsystems and heteroaromatic analogues thereof and substitutions thereof.

In a preferred embodiment, the flexible basestacking monomer is part of a oligonucleotide or oligonucleotide analogue.

In another preferred embodiment, the flexible basestacking monomer is adapted for incorporation into a oligonucleotide.

In a preferred embodiment, the flexible basestacking monomer adapted for incorporation into a oligonucleotide is selected from the group of a phosphoroamidite, a phosphordiamidite, a phosphordiester, a phosphortriester, a phosphonate, a H-phoshonate, a phosphite, a chlorophosphite, a chlorophosphoramidite, a phosphonamidite, a phosphonchloridite, a triphosphate, a diphosphate.

In still another embodiment, the flexible basestacking monomer of the invention can be described by the formula:

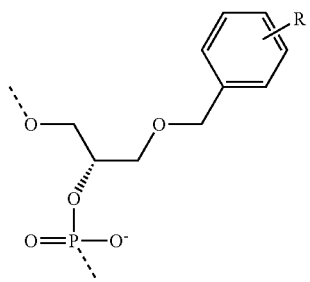

wherein R is selected from the group of arylethynyl.

Another aspect of the present invention is a oligonucleotide comprising the flexible basestacking monomer of the invention. The oligonucleotide may be any oligonucleotide that is capable of Watson-Crick base pairing and Hoogstein base pairing and reverse Hoogstein base pairing. The important point for oligonucleotides of the present invention is that they are capable of Watson-Crick base pairing and Hoogstein base pairing and reverse Hoogstein base pairing. Therefore, when the flexible basestacking monomer of the invention is incorporated into a oligonucleotide, the oligonucleotide becomes capable of triplex formation.

Another aspect of the invention is a method for preparation of a flexible basestacking monomer comprising the steps of Providing a precursor of a flexible basestacking monomer, wherein said precursor is a flexible basestacking monomer comprising $I_1$ substituted with a halogen or substituted with C or substituted with azide.

Replacing the halogen or the C substituent or the azide substituent of the precursor of step a with C-$I_2$ Making the C-$I_2$ substituted precursor of a flexible basestacking monomer adaptable for incorporation into a oligonucleotide Still another aspect of the invention is a method for preparation of a oligonucleotide comprising a flexible basestacking monomer comprising the steps of:

Providing a flexible basestacking monomer adapted for incorporation into a oligonucleotide Providing standard reagents for oligonucleotide synthesis During oligonucleotide synthesis incorporating one or more flexible basestacking monomers into the oligonucleotide Thereby generating a oligonucleotide comprising a flexible backbone monomer Still another aspect is a method for preparation of a oligonucleotide comprising a flexible basestacking monomer comprising the steps of:

Providing a precursor of a flexible monomer adapted for incorporation into a oligonucleotide, wherein said precursor is a flexible basestacking monomer comprising $I_1$ substituted with a halogen or substituted with C or substituted with azide.

Providing standard reagents for oligonucleotide synthesis

In another embodiment, the oligonucleotide comprising a flexible basestacking monomer is used as a medicament. The mechanism of action of such a medicament may be inhibition of the expression of a certain gene, i.e. by an antigenic mechanism. It could also be inhibition at the level of a mRNA or microRNAs.

Thus, the oligonucleotides of the invention may be used for the preparation of a medicament Items:
1. An intercalating oligonucleotide for stabilizing natural or modified DNA and RNA triplexes, duplexes and hybrids thereof having the general structure from formula 1.

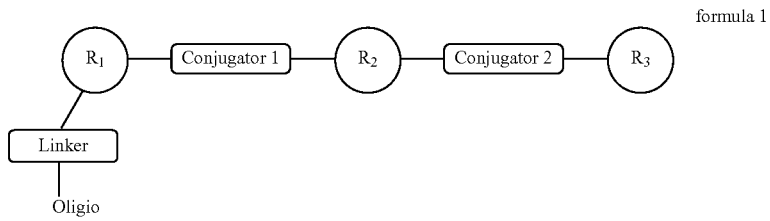

formula 1

During oligonucleotide synthesis incorporating one or more precursors of the flexible basestacking monomers into the oligonucleotide After synthesis of the oligonucleotide, the halogen substituent or the C substituent or the azide substituent on $I_1$ is replaced with C-$I_2$ Thereby generating a oligonucleotide comprising a flexible basestacking monomer A further aspect of the present invention is use of a oligonucleotide comprising the flexible basestacking monomer for formation of a triplex nucleic acid structure. As compared to traditional detection by hybridization, detection with a TFO does not require a denaturation step.

Thus, another aspect of the present invention is a method of forming duplex or triplex nucleic acids comprising the steps:
Providing an oligonucleotide according to claim 16
Providing a single stranded or a double stranded target nucleic acid
Incubating the oligonucleotide of step a with the single stranded or the double stranded target nucleic acid of step b under conditions of duplex or triplex formation
Thereby forming a double stranded nucleic acid or triplex nucleic acid structure Importantly, the TFO's of the present invention are capable of triplex formation at a pH of around 7, as will apparent from the examples section. This feature is very important for various application, e.g. for use as a medicament.

In a preferred embodiment, the formation of a triplex nucleic acid is used for sequence specific modulation of the activity of a target nucleic acid.

In preferred embodiments, the target nucleic acid is selected from the group of a chromosomal gene, an mRNA, an rRNA, a tRNA and a microRNAs or any precursors thereof. Thus, the triplex nucleic acid structure may inhibit translation of an mRNA, the function of an rRNA or a tRNA or the processing of a pre-miRNA to a mature microRNAs.

In other preferred embodiments, forming a triplex nucleic acid structure is used for sequence specific detection of the target nucleic acid.

Thus, it could be detection of a particular pre-cursor microRNA or detection of a particular gene-allele. Such detection methods are e.g. of interest for diagnostic purposes.

wherein
$R_1$, $R_2$ and $R_3$ are independently of each other a mono-cyclic or polycyclic aromatic ring system,
$R_1$, $R_2$ and $R_3$ may independently of each other be substituted
Oligo is an oligonucleotide consisting of subunits of DNA, RNA, PNA, HNA, MNA, ANA, LNA, CAN, INA, CeNA, TNA, (2'-NH)-TNA, (3'-NH)-TNA, α-L-Ribo-LNA, α-L-Xylo-LNA, β-D-Ribo-LNA, β-D-Xylo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, 2'-OR-RNA, 2'-AE-RNA, α-L-RNA, β-D-RNA, and modifications thereof. The subunits may contain modified nucleobases, carbohydrates, peptide chain. The oligonucleotide backbone may be modified.

Linker comprises of 1-60 atoms and it may contain non aromatic cyclic regions, wherein Oligo is connected via the linkage Linker to the aromatic ring system $R_1$ which in turn is connected via the Conjugator 1 defining a conjugated system, comprising a mono-cyclic and/or polycyclic aromatic ring system and/or alkyl, alkenyl and/or alkynyl, to the aromatic ring system $R_2$ which in turn is connected by the Conjugator 2 defining a conjugated system, comprising a mono-cyclic and/or polycyclic aromatic ring system and/or alkyl, alkenyl and/or alkynyl, to the aromatic ring system $R_3$, where Linker is a backbone monomer unit capable of being inserted into the backbone of a nucleic acid or nucleic acid analogue via a phosphate moieties, or a sugar moieties, or a nucleobases, or a modified oligo backbones.

Conjugated system comprising $R_1$, Conjugator 1, $R_2$, Conjugator 2 and $R_3$ can adopt a non-planar system.

An intercalating oligonucleotide according to claim 1, wherein the Conjugator 1 and Conjugator 2 are independently of each other. Conjugator 1 consists of an aryl, $R_4$, linked to $R_1$ via x single bonds, n double bonds and/or m triple bonds and linked to $R_2$ via y single bonds, k double bonds and/or l triple bonds where k, l, m, n, x and y independently from each other are integers of 0-5. Conjugator 2 consists of an aryl, $R_5$, linked to $R_2$ via z single bonds, p double bonds and/or r triple bonds and linked to $R_3$ via v single bonds, s double bonds and/or t triple bonds where p, r, s, t, v and z independently from each other are integers of 0-5. The so-formed conjugated system can form a non-planar system.

An intercalating oligonucleotide according to item 2, wherein aryl contains heteroatoms.

An intercalating oligonucleotide according to any of items 2 and 3, wherein $R_3$ has been replaced with a single atom as described in formula2. The conjugated system comprising $R_1$, Conjugator 1, $R_2$ and Conjugator 2 can adopt a non-planar system.

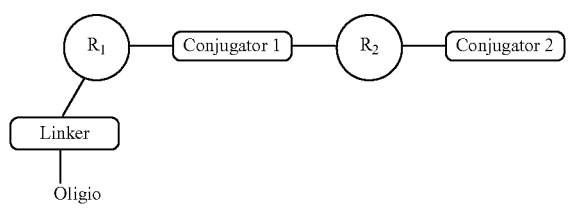

formula 2

An intercalating oligonucleotide according to any of items 2-4, wherein the Conjugator 1 and/or Conjugator 2 are independently selected from the group consisting of alkyl of from 1 to 12 carbons, alkenyl of from 2 to 12 carbons, alkynyl of from 2 to 25 carbons and combinations thereof.

An intercalating oligonucleotide according to any of items 2-5, wherein the alkynyl group is repetitive acetylenes.

An intercalating oligonucleotide according to any of items 2-5, wherein the alkynyl group is acetylene.

An intercalating oligonucleotide according to any of items 2-7, not containing $R_3$ and Conjugator-2 according to formula3.

formula 3

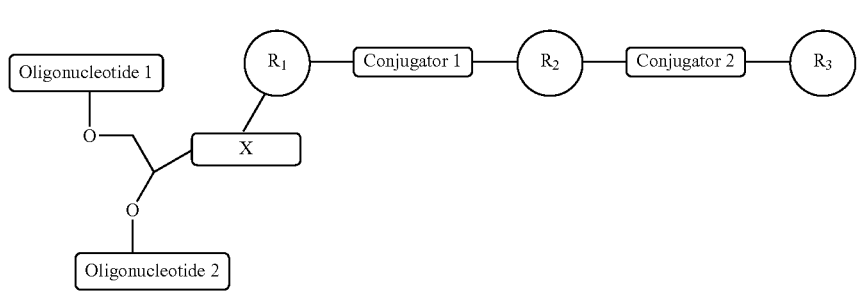

An intercalating oligonucleotide according to any one of the preceding items, wherein Linker is selected from the group consisting of straight-chain or branched-chain or cyclic groups An intercalating oligonucleotide according to item 9, wherein the straight-chain or branched-chain or cyclic group has heteroatoms selected from nitrogen, sulphur, phosphorous, and oxygen.

An intercalating oligonucleotide according to any one of the preceding items, wherein backbone monomer comprises ethylenglycol (formula4):

formula 4 wherein X consists of straight-chain or branched-chain or cyclic groups and Oligonucleotide 1 and Oligonucleotide 2 are defined independently of each other as Oligo in item 1.

An intercalating oligonucleotide according to item 11, wherein the straight-chain or branched-chain or cyclic groups has heteroatoms selected from nitrogen, sulphur, phosphorous, and oxygen.

An intercalating oligonucleotide according to any one of the preceding items, wherein backbone monomer comprises 1-O-methyleneglycerol (formula5):

formula 5

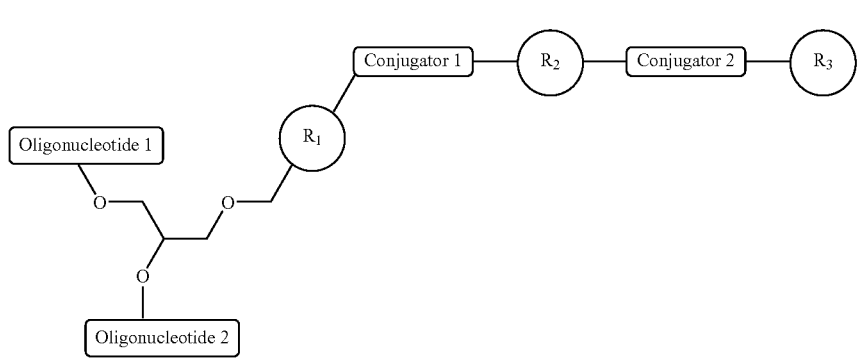

An intercalating oligonucleotide according to item 13, wherein $R_1$ consists of meta-, ortho- or para-substituted phenyl ring (formula6):

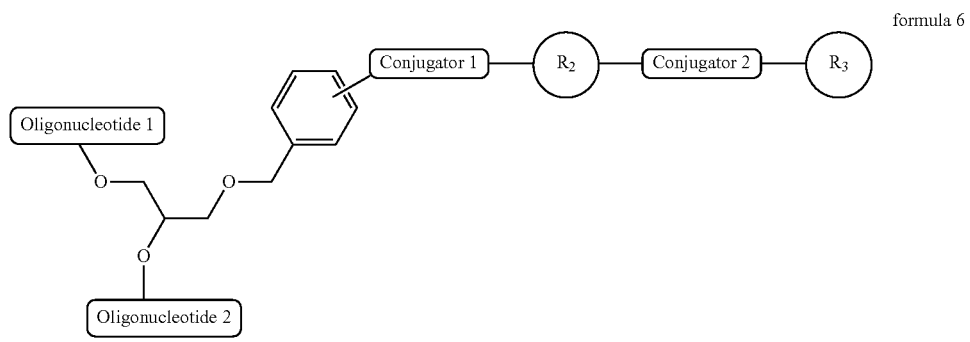

formula 6

An intercalating oligonucleotide according to item 14, wherein $R_2$ is pyrene without containing of $R_3$ and Conjugator 2 according to formula7.

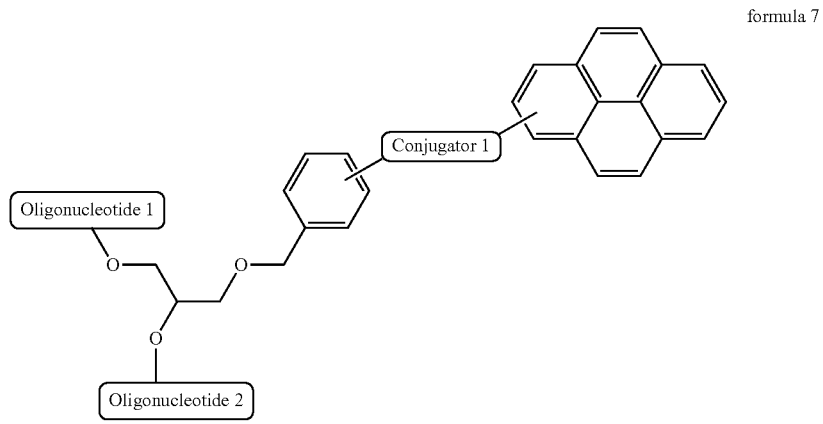

formula 7

An intercalating oligonucleotide according to item 15, wherein the Conjugator 1 consists of repetitive acetylenes or acetylene or aryl.

An intercalating oligonucleotide according to item 16, wherein aryl contains heteroatoms.

An intercalating oligonucleotide according to any of items 11-17, wherein substituted ethyleneglycole is a pure stereoisomer (R) or (S).

The intercalating oligonucleotides defined in formulas, where the Oligonucleotide 1 and Oligonucleotide 2 are defined independently of each other as Oligo in item 1.

formula 8

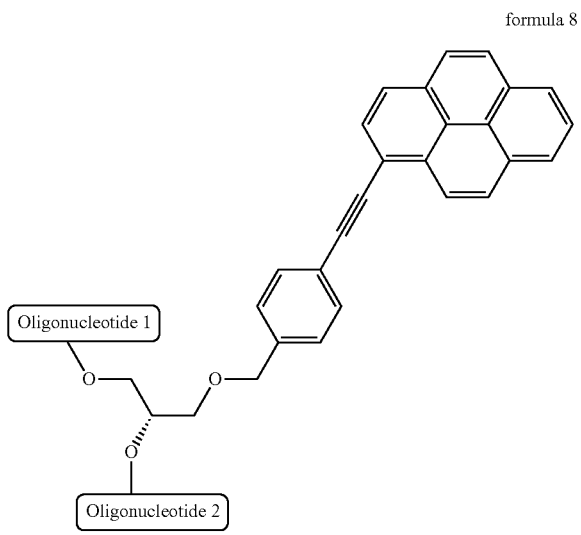 [SMILES: COC[C@H](COCc1ccc(C#Cc2ccc3ccc4cccc5ccc2c3c45)cc1)OC]

An intercalating oligonucleotide according to items 1-19, wherein Oligonucleotide 1 and Oligonucleotide 2 are single-stranded pyrimidin-rich oligodeoxynucleotides or oligoribonucleotides.

The Conjugator 1 and/or Conjugator 2 in intercalating oligonucleotide according to items 1-20 are assembled by post-synthetic synthesis of oligonucleotide possessing only a part of the final conjugated system (precursor intercalating oligonucleotide), eg. by Sonogashira coupling reaction (reaction between aryls having terminal acetylenes and halogen-aryl in the presence of Pd-catalyzator and/or CuI) or by Glazer reaction (reaction between aryls possessing terminal acetylenes in the presence of cupper ions) or by click-chemistry (reaction between organic azides and organic molecules possessing terminal acetylenes in the presence of copper ions).

The synthesis according to item 21 is performed on the precursor intercalating oligonucleotide possessing acid and/or base labial protective group.

The synthesis according to item 21 may be performed on the unprotected precursor intercalating oligonucleotide.

The precursor intercalating oligonucleotide according to items 22 and 23 is attached to the solid support.

A method according to the item 24, wherein the solid support is an activated surface.

A method according to the item 24, wherein the solid support is a selected from the group consisting of magnetic beads, agarose beads, sepharose beads, glass, plastic surfaces, heavy metals and chip surfaces.

The intercalating oligonucleotide of items 1-20 is obtained by stepwise oligonucleotide synthesis using the monomer of Linker connected to the final conjugated system or to a part of the final conjugated system. The Linker possess at least two reactive groups, said reactive groups may optionally react with growing chain of oligonucleotide or oligonucleotide analogue. The said monomer is capable to react with a growing chain of a support-bound nucleotide, oligonucleotide, nucleotide analogue or oligonucleotide analogue and optionally further elongating said oligonucleotide of oligonucleotide analogue by adding one or more nucleotides, nucleotide analogues to the oligonucleotide analogue in a desired sequence; and cleaving said oligonucleotide or oligonucleotide analogue from said solid support; and cleaving base/acid labile protective groups thereby obtaining the intercalating oligonucleotide.

The intercalating oligonucleotide of items 1-20 is capable of forming Hoogsteen triplex or reverse Hoogsteen triplex with one of the duplex strands, the duplex being a DNA duplex, RNA duplex or hybrids thereof. The Oligo parts of the intercalating oligonucleotide of item 1-20 is capable of forming Hoogsteen duplex, or reverse Hoogsteen duplex or Watson-Crick duplex with one of the single strands, the single strand being a DNA, RNA or hybrids thereof.

Hoogsteen triplexes and Hoogsteen duplexes shows increased thermal stabilities, when the monomer comprising $R_1$, Conjugator 1, and $R_2$ and eventually Conjugator 2 and $R_3$ according to items 1-20, forms a bulge.

The intercalating oligonucleotides of items 1-20 are conjugated to DNA reactive agents. DNA reactive agents are mutagenic agents capable of directing mutagenesis, or are photoinducable crosslinkers, or are radioactive agents, or are alkylating groups, or are molecules that can recruit DNA-damaging cellular enzymes.

A pharmaceutical composition suitable for use in antisense therapy and antigene therapy, which composition contains, as intercalating oligonucleotides of items 1-20.

A method to treat diseases or conditions mediated by the presence of unwanted duplex oligonucleotides, which method comprises administering to a subject in a need of such treatment an effective amount of the oligonucleotide of items 1-20 or a pharmaceutical composition thereof.

A method to perform chemoselective ligation using the intercalating oligonucleotides of items 1-20 conjugated to DNA reactive groups on a template comprising a DNA, RNA or hybrids thereof. DNA reactive groups are chemical groups capable to react with other chemical groups under appropriate conditions.

A method according to item 33 wherein the chemoselective ligation is bioorthogonal. A method according to item 34 wherein one of the DNA reactive groups is azide or terminal acetylene or phosphane.

The intercalating oligonucleotide of items 1-20 can be used for purification of DNA plasmids (double-stranded DNA).

The intercalating oligonucleotide of items 1-20 can inhibit transcription.

The intercalating oligonucleotide of items 1-20 can be used for Fluorescence In Situ Hybridization (FISH) and analogues of this method, eg. multiplex (multicolor) Fluorescence In Situ Hybridization (M-FISH), conventional FISH, COMBO-FISH etc.

The intercalating oligonucleotide of items 1-20 can be used for gene repair.

The intercalating oligonucleotide of items 1-20 can be used in a nucleic acids nanomachine based on a duplex-triplex transition, wherein nucleic acids are defined as Oligo in item 1.

The intercalating oligonucleotide of items 1-20 can be used in a nucleic acids nanomachine based on a parallel duplex-antiparallel duplex transition, wherein nucleic acids are defined as Oligo in item 1.

The intercalating oligonucleotide of items 1-20, wherein fluorescence properties is altered upon hybridization to a corresponding DNA, RNA and analogues thereof.

A system wherein the intercalating oligonucleotide of items 1-20 is attached to the solid support.

A system according to the item 43, wherein the solid support is an activated surface.

A system according to the item 43, wherein the solid support is a selected from the group consisting of magnetic beads, agarose beads, sepharose beads, glass, plastic surfaces, heavy metals and chip surfaces.

Figure 1:
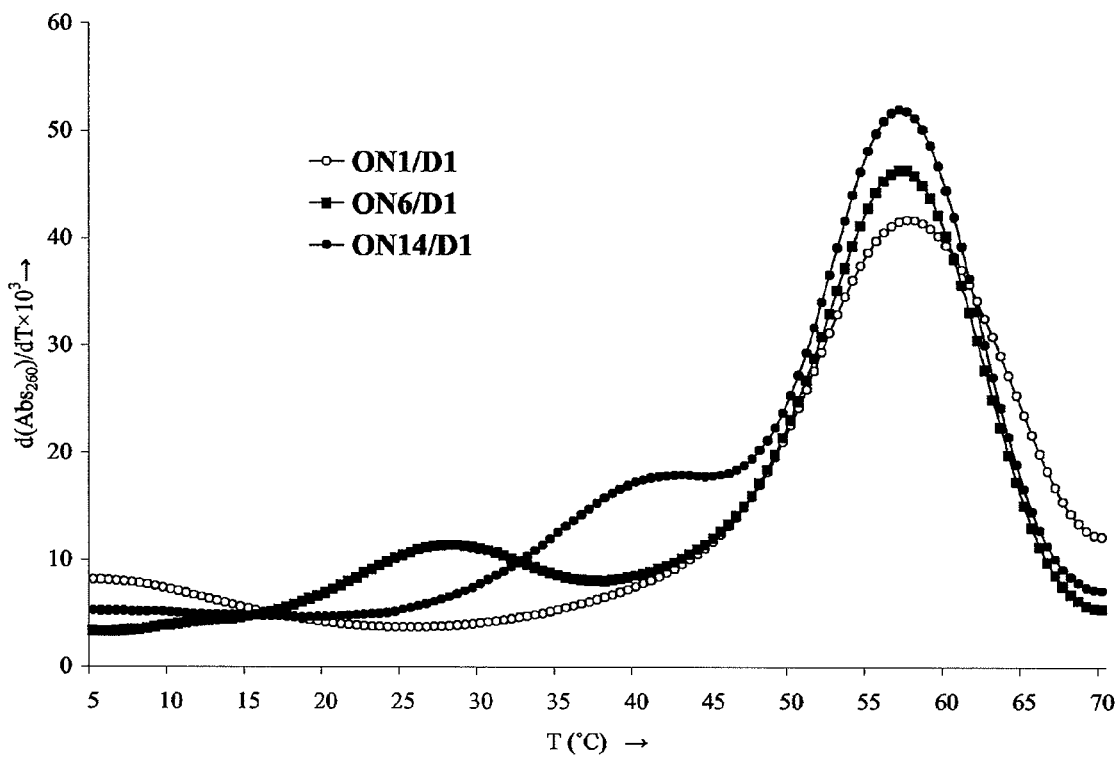
FIG. 1

The first derivative plots of triplex melting recorded at 260 nm versus increasing temperature (1° C./min) in 20 mM sodium cacodylate, 100 mM NaCl, 10 mM MgCl$_2$, pH 7.2.

FIG. 2-6

Fluorescence spectra of single-strands, antiparallel and parallel duplexes, and parallel triplexes. Measurement conditions: 1 μM of each strand in a buffer at 10° C. (20 mM sodium cacodylate, 100 mM NaCl, 10 mM MgCl$_2$, pH 6.0), excitation: 373 nm (excitation slit 4.0 nm), emission: 380-600 nm (emission slit 2.5 nm for A, B, E, and 0.0 nm for C and D). ON6 and ON12 were used as references in spectra recorded under different conditions.

EXAMPLES

Example 1

Recently, we have reported the synthesis and properties of several intercalating nucleic acids designed for Watson-Crick type duplexes (Scheme 1).[9] Bulged insertions of (R)-1-O-(1-pyrenylmethyl)glycerol in the middle of the oligodeoxynucleotides (INA®) resulted in significantly increased affinities towards complementary ssDNA, whereas INA/RNA duplexes and Hoogsteen-type triplex and duplex were destabilized.[9a,e] It has to be also mentioned that mis-match sensitivity on duplex formation was maintained upon bulged insertions of intercalators into the oligodeoxynucleotides.[9b] The unique combination of the flexible, short glycerol linker which distorted the phosphate backbone and the appropriate intercalator which stabilized INA/DNA duplex by desolvation and by stacking with nucleobases led to a valuable molecule which is now used in nucleic acid chemical biology.

We decided to explore this type of intercalators for the design of TFO. In order to enhance the stability of the TFO using a short and flexible linker, the aromatic structure of intercalators should be long enough to place an intercalator into the dsDNA part of the triple helix. Therefore (R)-1-O-(4-polyaryl-phenyl)methylglycerol could be a good choice because phenyl could also mimic a nucleobase in the TFO part of the triple helix. The polyaryl intercalator can also be attached to this phenyl via an acetylene bridge which provides the necessary structural rigidity and twisting flexibility and still unites the aromatic structures. The acetylene bond itself is believed to improve the intercalating properties. According to the molecular modeling of (R)-1-O-[4-(1-pyrenylethynyl)-phenylmethyl]glycerol by MacroModel 8.0, there is a twisting of 1-pyrenyl and phenyl residues around the triple bond with a torsion angle of 15.3°. It is believed that this twisting ability can help the intercalator to adjust itself to an appropriate position inside the dsDNA. Therefore, we refer to this type of nucleic acids as twisted intercalating nucleic acids (TINA, Scheme 1). Here we report the post-synthetic Sonogashira-type on-column derivatization of oligodeoxynucleotides leading to different TINAs, which were found to have extraordinarily high affinities in Hoogsteen-type duplexes and triplexes. Thermal stability and fluorescence studies of nucleic acid helixes with insertion of TINA as a bulge formed according to either Watson-Crick or Hoogsteen binding modes are also presented.

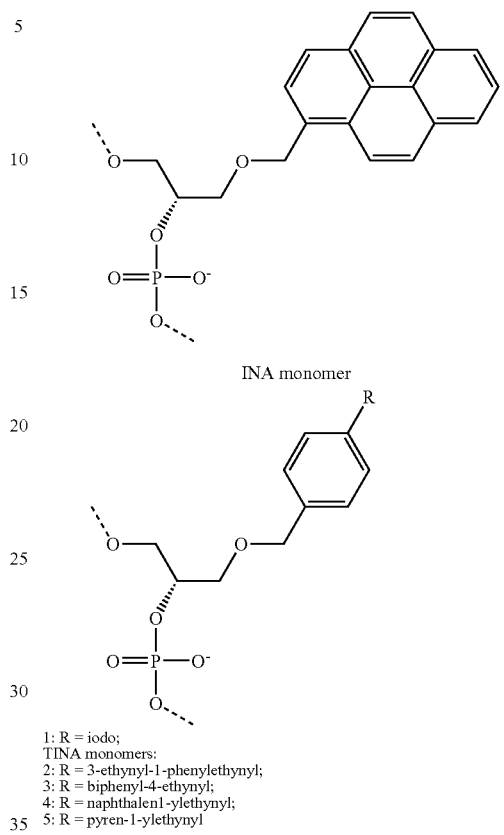

Scheme 1 Chemical structures of monomers of intercalating nucleic acid (INA) and twisted intercalating nucleic acid (TINA)

1: R = iodo;
TINA monomers:
2: R = 3-ethynyl-1-phenylethynyl;
3: R = biphenyl-4-ethynyl;
4: R = naphthalen1-ylethynyl;
5: R = pyren-1-ylethynyl The post-synthetic oligonucleotide modification is a better alternative to the routine and time-consuming preparation of several pseudo-nucleoside phosphoramidites, which are required for the selection of the right candidate for TINA. There have been several reports devoted to the palladium(0)-catalyzed modification of oligonucleotides during solid-phase synthesis. Sonogashira coupling conditions were found to be compatible with the DNA synthesis and no side reactions were observed for nucleobases possessing protective groups. According to the known protocols the DNA synthesis is stopped after the incorporation of 5'-O-DMT-2'-deoxy-5-iodouridine at the 5'-end of the sequence followed by treatment of the oligonucleotide support under Sonogashira conditions. Afterwards the oligo synthesis is continued to the end. However, not all functional groups could survive after insertions during the continued oligonucleotide synthesis. There is a risk that the coupling efficiency for the standard phosphoramidates drops after on-column derivatization, which we have also observed in our experiments described below. Despite the fact that some organometallic couplings were applied for post-synthetic oligonucleotide modification, the post-synthetic Sonogoshira-type reactions on the convertible nucleoside 2'-deoxy-5-iodouridine located in the middle of the sequence were reported unsuccessful. Instead we took a chance to use (R)-1-O-(4-iodobenzyl)glycerol in Sonogoshira-type reactions after its incorporation into the middle of the oligos. A number of aromatic structures with the terminal triple bond (2-5) were used in this context (Scheme 1).

The required phosphoramidite 8 was synthesized in four steps from 4-iodobenzylbromide and (S)-(+)-2,2-dimethyl-1, 3-dioxolane-4-methanol in 47% overall yield (Scheme 2, see Supporting Information for experimental details). The coupling efficiency of compound 8 during DNA synthesis in 0.2 μmol-scale using standard nucleotide coupling conditions (2 min coupling, 4,5-dicyanoimidazole as an activator) and increased deprotection time (100 sec) was estimated to be more than 99%. After the DNA synthesis, the CPG-supports with DMT-on oligonucleotides possessing 4-iodophenyl moieties were treated with a Sonogashira-coupling reagent mixture containing Pd(PPh$_3$)$_4$ or Pd(PPh$_3$)$_2$Cl$_2$ (7.5 mM), an aromatic structure possessing a terminal acetylene (22.5 mM), and CuI (7.5 mM) in dry DMF/Et$_3$N (3.5/1.5, 500 μL) in 1 mL syringes under dry conditions at room temperature. It was important to flush supports and syringes with argon instead of nitrogen prior to the coupling reaction in order to avoid Glazer oxidative dimerization. The conversion was found better when the Sonogashira reaction mixture was prepared directly in the plastic syringe for each individual oligo instead of preparation of the Sonogashira reaction mixture as a large portion for several coupling reactions. After the coupling reaction (3-4 h), the CPGs were flushed with DMF (2×0.5 mL) and CH$_3$CN (2×1 mL), and dried. Then the oligonucleotides were cleaved off from the CPG-support with 32% NH$_4$OH (2 h), and deprotected at 55° C. (overnight). Due to the different lypophilic ability, the unreacted oligomer and the target TINA were separated by semi preparative HPLC on a C$_{18}$ column. In case of the overlapping peaks (structure 2) a longer HPLC-program was applied (see Supporting Information). After the first separation DMT-on oligonucleotides were treated with 10% AcOH, purified again on HPLC and precipitated from ethanol. A purity of the final TFOs was found to be over 90% for pure pyrimidine containing oligodeoxynucleotides and 85-88% for oligodeoxynucleotides with purines as judged by ion-exchange HPLC. The composition was verified by MALDI-TOF.

Scheme 2. Synthesis of the phosphoramidite 8.

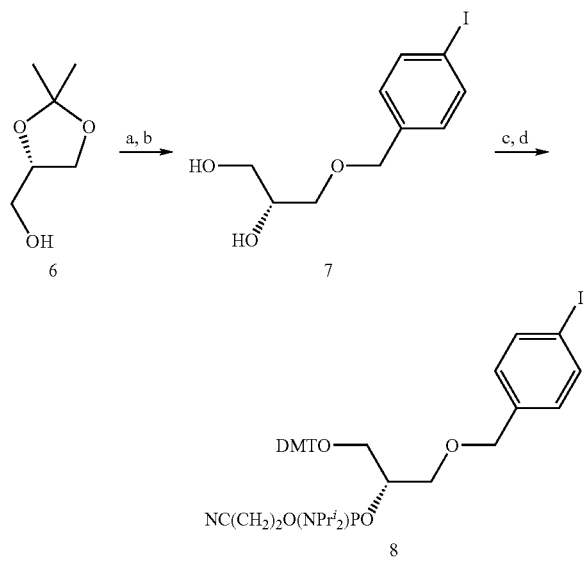

Reagents and conditions: (a) 4-iodobenzylbromide, KOH, toluene; (b) 80% aq. CF$_3$COOH, rt, 100% over two steps; (c) DMTCl, pyridine, rt, 70%; (d) NC(CH$_2$)$_2$OP(NPr$^i$$_2$)$_2$, diisopropylammonium tetrazolide, CH$_2$Cl$_2$, 0° C. to rt, overnight, 67%.

The conversion during the Sonogashira coupling depended on the reactivity of acetylenes and on the oligo sequence. As can be judged from a number of experiments with 1-ethynylpyrene, one more treatment with the fresh reaction mixture was more efficient than the prolonged reaction time (4-16 h). Less amount of sparingly soluble Glazer byproducts, were formed and better oligo derivatization was observed for Pd(PPh$_3$)$_4$ than for Pd(PPh$_3$)$_2$Cl$_2$ as the catalyst in the case of 1-ethynylpyrene. The presence of purines in the sequence resulted in lower conversion (50-60%) to the target TINA even after double treatment of the support with the oligonucleotide by the Sonogashira-coupling reagent mixture containing 1-ethynylpyrene compared to the homopyrimidine sequences (80-85%) after a single treatment. This also seems true for other aromatic acetylenes, because in a purine containing sequence no target oligonucleotides were obtained using 4-ethynylbiphenyl, which was found the least reactive compound among the tested acetylenes. In the synthesis of ON14 we experienced that the treatment of a complete oligonucleotide with a Sonogashira reaction mixture with 1-ethynylpyrene gave a more pure oligomer than interruption of the DNA synthesis after the second insertion of 8 followed by Sonogashira reaction and continued DNA synthesis. In the latter case short oligomers possessing pyrenes contaminated the final TINA as judged by ion-exchange HPLC.

Very recently copper-free Sonogashira coupling reaction with PdCl$_2$ in water in the presence of pyrrolidine was reported. The compatibility with water, aerobic conditions and traces of homocoupling products are the very big advantages of this method. We applied the analogues conditions on the fully deprotected ON2. However, after treatment of ON2 with 1-ethynylnaphthalene and PdCl$_2$ in water/pyrrolidine (1:1) at 50° C. or 20° C. overnight, no trace of the desired nucleic acids was observed after HPLC purification.

The thermal stability of triplexes, DNA/DNA and DNA/RNA duplexes with the synthesized oligonucleotides were assessed by thermal denaturation experiments. The melting temperatures (T$_m$, ° C.) determined as first derivatives of melting curves are listed in Tables 1-4. The sequences possessing different TINAs were studied in pH dependent Hoogsteen-type base pairing, both in parallel triplex towards the duplex D1 and in parallel dsDNA towards ON15 (Table 1). The same sequences (ON1-14) were used for Watson-Crick DNA/DNA antiparallel duplexes towards ON16. For the latter type of duplexes mixed pyrimidine/purine sequences similar to those described earlier for INA were also used for TINA oligonucleotides for hybridization with ssDNA and ssRNA (Table 4).

As can be seen from the T$_m$ data in Table 1, considerable destabilization of the Hoogsteen-type triplex and duplex was observed for ON2 with (R)-1-O-(4-iodophenylmethyl)glycerol as a bulge in the middle of the sequence compared to the wild-type complexes at pH 6.0 (ON1 towards D1 and ON15). Substitution of the iodine with aryl substituents gave more stable triplexes (ON3-ON6 towards D1, pH 6.0). The highest T$_m$ value 46.0° C. was observed for the 1-pyrenylethynyl substituent at pH 6.0 which corresponds to ΔT$_m$=19.0° C. when compared to the wild-type triplex. Even at pH 7.2 a single incorporation of 5 led to a considerable stabilization of the triplex (ON6/D1), in spite of a high cytosine content (36%). At this pH no hybridization could be detected for the wild-type triplex (FIG. 1). For the parallel duplexes at pH 6.0 the stabilization of 3.0° C. and 14.5° C. per modification was detected for 1-naphthalenylethynyl (ON5) and 1-pyrenylethynyl (ON6), respectively. As expected, at lower pH (pH=5.0) parallel duplexes were found more stable due to protonation of cytosine. It could be concluded that attaching of the aromatic structures at 4-position of the phenyl ring in (R)-1-O-(phenylmethyl)glycerol resulted in increasing hybridization affinity in Hoogsteen-type helixes. Interestingly, naphthalene and pyrene rings gave considerably better stabilization than 4-biphenyl and benzene. This supports the idea that aromatic structures with a large surface such as pyrene is preferred for attachment to (R)-1-O-(4-substituted phenylmethyl)glycerol over small aromatic structures to achieve good binding in Hoogsteen-type helixes.

Destabilization of antiparallel dsDNA was observed for all studied modified oligodeoxynucleotides except when the intercalator 5 was placed at 5'-end (ON10/ON16) as compared with the wild-type dsDNA (ON1/ON16, Table 1). The stabilizing effect in the latter case could be ascribed to stacking of an aromatic polycyclic system on the adjacent nucleobase (the effect as a lid), while the effect of the acyclic linker is marginal. Hybridization affinity was also dependent on the structure of TINA. The least destabilized duplexes were formed with 4 and 5, whereas the destabilization of dsDNA was larger for structures 1-3 incorporated as a bulge in the middle of the sequence. Already at this stage it can be concluded that TINA incorporated as a bulge into helixes is improving the stability of Hoogsteen-type helixes and not Watson-Crick type duplexes. Thus a single insertion of (R)-1-O-[4-(1-pyrenylethynyl)phenylmethyl]glycerol as a bulge in a less stable parallel triplex (ON6/D1) at pH 6.0 stabilized the triplex to the level of a Watson-Crick duplex (ON6/ON16) with the same nucleotide content. The thermal stability for different TINAs, prompted us to investigate the properties of the 1-pyrenylethynyl containing TINA more closely.

Some fluctuation in the thermal stability of Hoogsteen's triplexes and duplexes was seen on placing 1-pyrenylethynyl at different positions in the TFO. When cytosine was neighboring either the 5'- or the 3'-sides (ON7-ON9), both the parallel triplex and the parallel duplex were less stabilized than when 5 was placed between two thymidines at pH 6.0 (ON6). This could be a result of the interaction of the aromatic structure with the positively charged pair of $C^+ \cdot G$. Interestingly, at pH 7.2, when cytosine was not protonated, the lowest triplex hybridization affinity was detected for TFO with 5 at 5'-dangling end (ON10) among the tested TFOs with single insertion of 1-pyrenylethynyl (ON6-ON10). It was a surprise that the lid effect was absent here. This could be a consequence of generally lower stability of C-rich regions of TFO with the target dsDNA under physiological conditions. However, it is an important observation that efficient hybridization affinity could be achieved by placing 5 in the middle of the C-rich region (ON9) in neutral media. One can speculate whether intercalation will make protonation more likely in the triplex structure at physiological pH because the intercalator is separating two positively charged triples.

The dependence of the distance between multiple bulged insertions of the pyrene intercalator 5 on thermal stability was investigated using ON11-ON14 (Table 1). In case of overlapping triplex and duplex transitions, melting experiments were performed at 373 nm. However, sometimes not very well defined transitions were observed at 373 nm. In these cases the assumption about meltings at pH 6.0 of the triplexes at temperatures close to those of the duplexes were based on comparison with meltings at pH 7.2 which were measured at 260 nm. When the intercalator 5 was inserted as a next nearest neighbors (ON12), the Hoogsteen triplex and duplex were stabilized compared to the unmodified ON1 at pH 6.0. However, the stabilities in both cases were lower than for the single insertion of 5 (ON6) and no triplex formation was observed at pH 7.2. This could be due to the large interruption of the double and triple helixes by two bulged (R)-1-O-methylglycerol linkers positioned very close to each other. When the two insertions of 5 were separated by two or three nucleobases (ON13 and ON14, respectively), the complexes with D1 and ON15 were more stable than those with single insertions. At pH 7.2 the $T_m$ for the triplexes was even higher than the physiological temperature 37° C. (see ON14/D1 in FIG. 1). Like double insertions of 5 in the middle, double insertions with one insertion at the 5'-end with six base-pairs between the insertions (ON11) considerably stabilized Hoogsteen-type duplex and triplex at pH 6.0. Opposite to the Hoogsteen helixes, antiparallel duplexes with double insertions of 5 (ON12-14/ON16) showed decreased stabilities when compared with the wild-type duplex ON1/ON16, especially when one or three nucleobases were between the two insertions. When comparing thermal stabilities of parallel and antiparallel duplexes with double insertions of 5 at pH 5.0, Hoogsteen duplexes ON11/ON15 and ON14/ON15 were even more stable than the corresponding Watson-Crick duplexes (ON11/ON16 and ON14/ON16). The stabilization of parallel triplexes and parallel duplexes upon addition of an intercalator was first reported for benzopyridoindole (BPI) derivatives. The reorganization of non-perfectly matched Watson-Crick DNA duplex into perfectly matched Hoogsteen paired DNA duplex has been detected when BPI was added to the aqueous solution of the oligodeoxynucleotides. A similar effect is anticipated in favor for fully matched parallel duplex on insertions of 5 into oligodeoxynucleotides.

The extraordinary stabilization of parallel triplexes was observed at pH 5.0. High content of cytosines in the TFO shifted the melting of the unmodified triplex ($T_m$=55.0° C.) close to the melting of the duplex. However, this value was still lower than the duplex melting at pH 5.0 ($T_{m(D1)}$=56.5° C.). Single bulged insertion of 1-naphthalenylethynyl derivative 4 in the TFO slightly increased the triplex stability ($\Delta T_m$ $_{(ON5/D1-ON1/D1)}$=2.0° C.). However, bulged insertion of 5 in all cases led the dissociation of the whole complex at temperatures which were higher than $T_m$ for the dsDNA (D1). The clear transition state for ON11 was observed at 373 nm at the same temperature as at 260 nm, which confirmed that the triplex and the duplex melted together. The same dependence of thermal stability for double insertion of 5 in TFO as at pH 6.0 was observed at pH 5.0. Thus, the double insertion of 5 as next-nearest neighbors (ON12) and insertions of 5 in the middle and at the 5-end (ON11) were the least and the most stabilized triplexes, respectively. At pH 5.0, the triplex ON14/D1 was 16.5° C. and 20.5° C. more stable than the corresponding parallel and antiparallel duplexes, respectively. Importantly that even at pH 7.2 oligonucleotide ON14 forms more stable Hoogsteen-type triplex ($T_m$=43.0° C., ON14/D1) than the corresponding Watson Crick dsDNA ($T_m$=38.0° C., ON14/ON16). At pH 7.2 the melting temperature for the parallel duplex (ON14/ON15) supposes to be lower than 38.0° C. observed at pH 6.0 since this duplex is pH-sensitive. This data clearly demonstrate the ability of oligonucleotides with multiple insertions of 5 in the middle of the sequence separated by three bases to discriminate well between dsDNA and ssDNA.

The sensitivity to mis-matches was studied for parallel triplexes and duplexes with bulged insertion of 5 in the middle and at the 5'-end of the sequence (Table 2). In case of triplexes the sensitivity to mis-match was dependent on the site of insertion of the intercalator. The smallest value of $\Delta T_m$=11.5° C. between matched and mis-matched triplexes was detected when adenine was replaced by guanine in the purine strand on the 3'-site of the intercalator (ON6/D3 and ON11/D3, Table 2). In all other cases the dropping of $T_m$ was in a range of 14.0-22.0° C. Mismatched parallel duplexes with a single insertion of 5 were destabilized in the range of 8.0-13.0° C. which was in the same range as mis-matched wild type parallel duplexes. For comparison the least sensitive mismatched unmodified duplex showed a $\Delta T_m$ of 9° C. at pH 6.0 ($T_{m(ON1/ON15)}$-$T_{m(ON1/ON18)}$).

Figure 2:
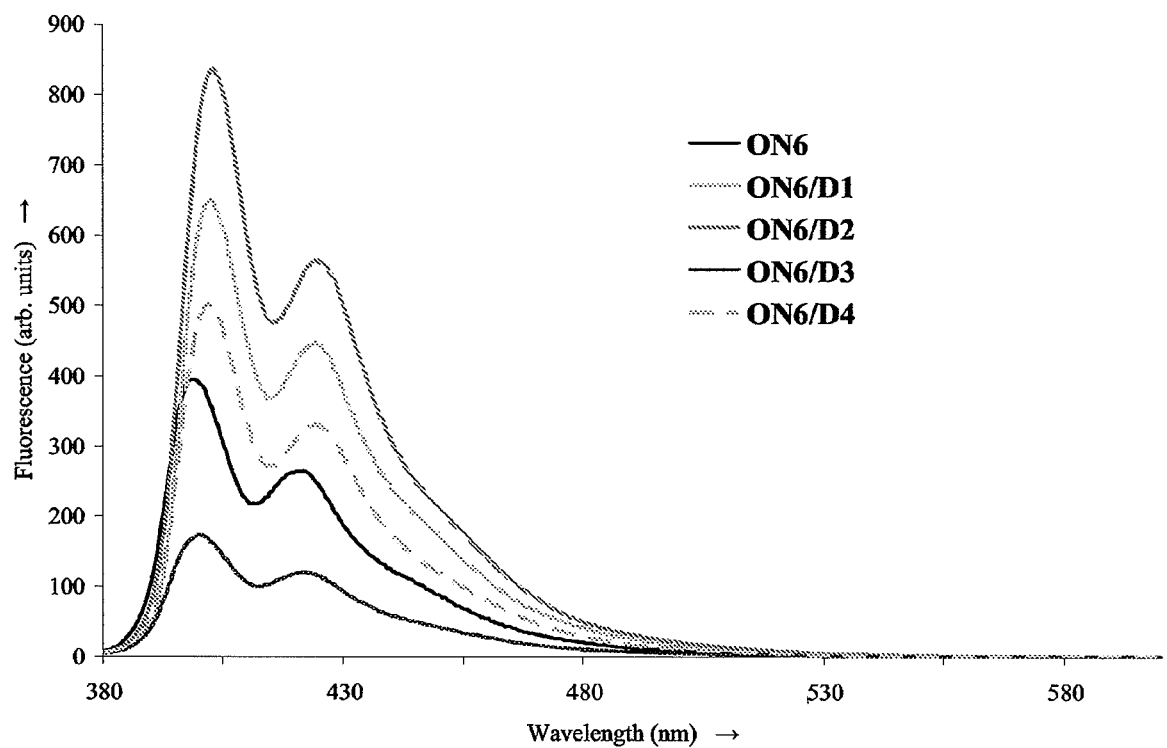

We studied the luminescent characteristics of the TFO possessing (R)-1-O-[4-(1-pyrenylethynyl)phenylmethyl]glycerol (5) which was the most effective TINA to form triplexes and to discriminate mismatches to the duplex. The introduction of 5 into oligonucleotides resulted in a characteristic monomeric fluorescence spectrum, with maxima at 400 and 421 nm upon excitation at 373 nm (FIG. 2, black curve), which was similar to previously published data for 4-[4-(1-pyrenylethynyl)phenyl]-1,3-butanediol inserted into DNA.[18] In all cases a 4 nm shift of monomeric fluorescence was detected upon formation of triplexes or duplexes. Formation of the fully matched triplex led to approximately 1.5 fold increased monomeric fluorescence (FIG. 2, ON6/D1) compared to the single-stranded ON6. For non-perfectly matched triplexes the fluorescence intensity depended on the sequence of dsDNA. Thus almost twofold increase was detected for a TA inversion site (ON6/D2) compared to ON6. On the contrary, when a cytosine or a guanine base was mis-matching in dsDNA to the TFO near the insertion of 5 (D3 and D4), a decrease of monomeric fluorescence was seen in comparison with the perfectly matched triplex (FIG. 2). Especially guanine gave a large effect with twofold lower fluorescence intensity for the mis-matched triplex ON6/D3.

Figure 3:
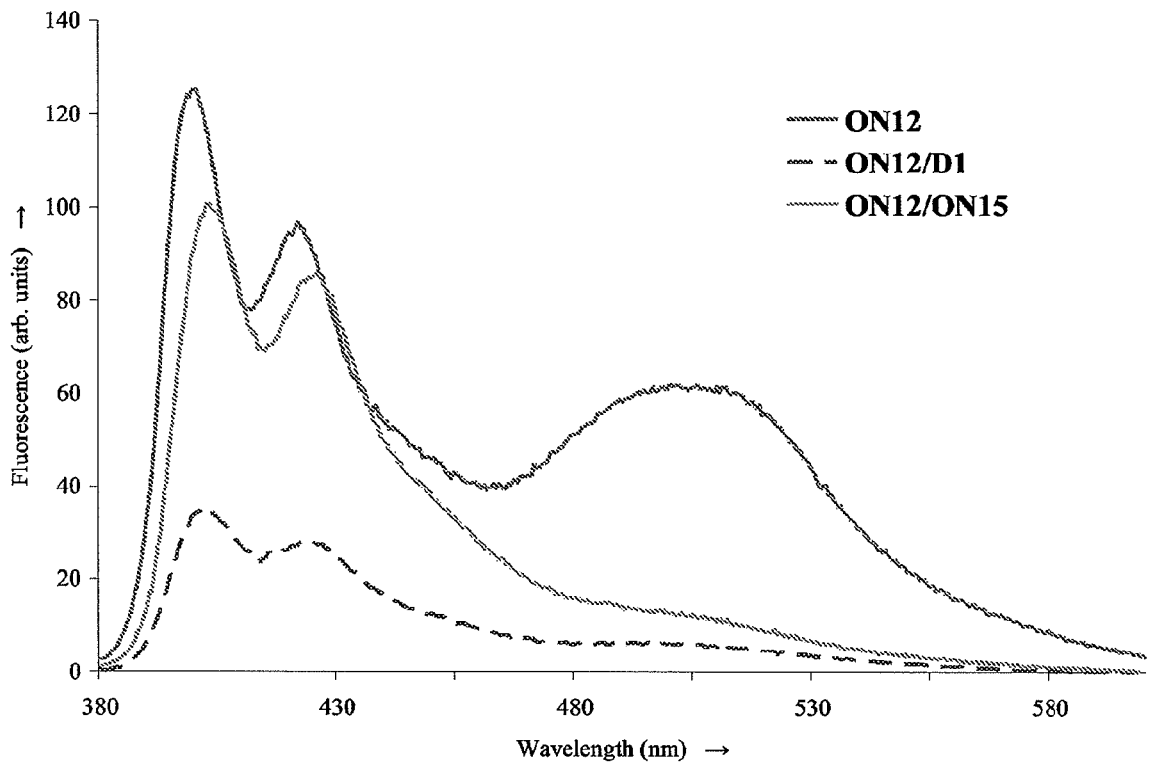
Figure 4:
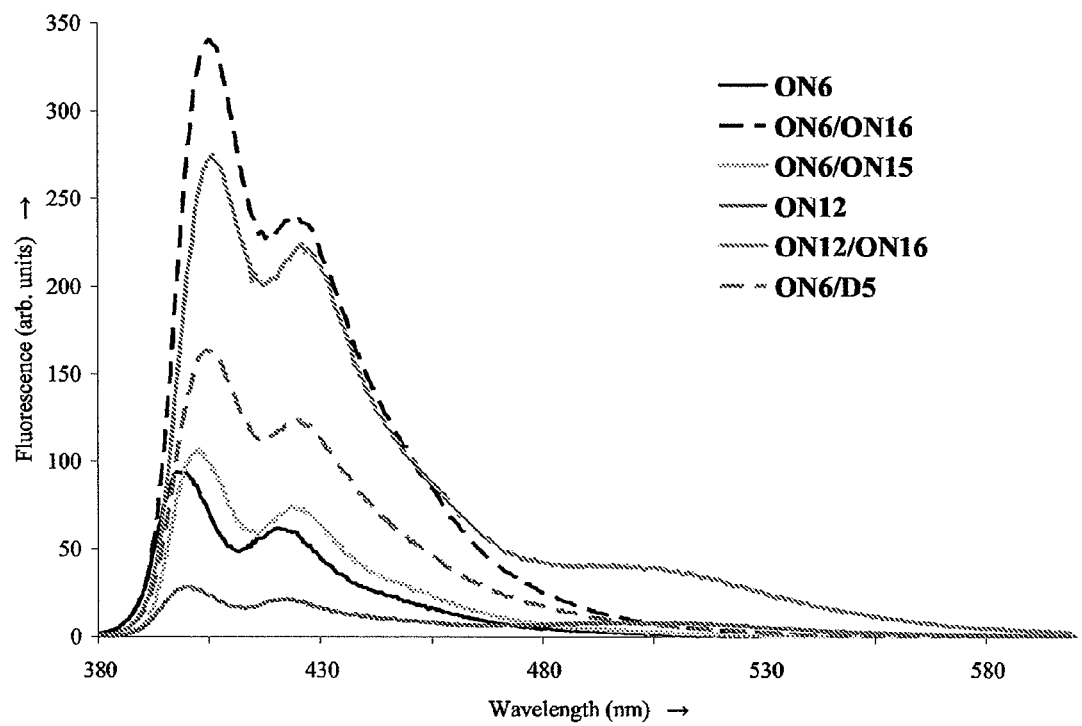

Interestingly, a considerable increase in monomer fluorescence was detected upon formation of the antiparallel duplex (ON6/ON16, FIG. 4), whereas the formation of the parallel duplex (ON6/ON15) resulted in only a slightly increased fluorescence when compared with the single strand fluorescence (FIG. 4). When a second 4-(1-pyrenylethynyl)phenyl residue appeared as a next-nearest neighbor in ON12, the monomeric fluorescence of the single strand decreased approximately threefold (FIG. 4, comparison of ON6 and ON12), and an excimer fluorescence with a maximum at 500 nm and with an intensity half of that of the monomeric intensity could be observed (FIG. 3). A considerable decrease of the monomeric fluorescence and disappearance of the excimer band was observed for the same oligo in a matched triplex (FIG. 3, ON12/D1). This means that the pyrene moieties could not communicate with each other upon binding to dsDNA in the environment of the triplex helix. Similarly, the excimer band disappeared when ON12 formed a Hoogsteen-paired dsDNA with ON15 (FIG. 3). On the contrary, very high monomeric fluorescence intensity and increased excimer fluorescence were observed for the antiparallel duplex (ON12/ON16) when compared with fluorescence intensities of the single stranded ON12 (FIG. 4). This indicates that the two pyrenyls in the same strand were still in a close contact with each other after formation of the Watson-Crick dsDNA although this seems not the case in the Hoogsteen-type dsDNA. In this way the different properties of TINA towards Watson-Crick and Hoogsteen type helixes was reflected by both hybridization and fluorescence properties. Moreover, fluorescence data for (R)-1-O-[4-(1-pyrenylethynyl)phenylmethyl]glycerol (5) as bulged next-nearest neighbors in pyrimidine rich strand can be summarized as follows: single-strand ON12: medium monomer fluorescence at 400 and 421 nm and excimer band at 500 nm; parallel triplex ON12/D1: low monomer fluorescence and no excimer band; parallel duplex ON12/ON15: medium monomer fluorescence and no excimer band; antiparallel duplex ON12/ON16: high monomer fluorescence and excimer band.

The ability of the structure 5 to affect the stability of the parallel triple helix upon its incorporation into the Watson-Crick duplex part of the triplex is presented in Table 3. The triplex was stabilized in all cases when 5 was inserted as a bulge in the pyrimidine strand of the duplex (ON1, ON6 and ON9 towards D5) when compared to the unmodified triplex (ON1/D1). Two transition states ($T_m$=36.5° C. and 55.5° C.) were detected for the triplex ON1/D1 in the thermal denaturation experiment at 373 nm [$\lambda_{max}$ of 5] which corresponded to triplex and duplex meltings, respectively. Detection of the meltings by the 373 nm absorbance indicated that the intercalator was involved both in the duplex and triplex formation. The insertion of 5 as bulges in both Watson-Crick and Hoogsteen pyrimidine strands opposite to each other (ON6/D5) did not change the melting of the triplex when compared with a triplex with an intercalator only in the duplex part of the triplex (ON1/D5). When two pyrene moieties 5, one in each of the pyrimidine strands, were placed as bulges separated by three base-pairs (ON9/D5), the triplex melting was very close to the duplex transition state, which was also observed above for the double incorporation of 5 into TFO. Decreased triplex and parallel duplex stabilities compared to the unmodified complexes were observed when compound 5 was inserted in the purine strand as a bulge (ON1 towards D6 and towards ON21).

We also studied the hybridization affinity of TINA possessing 5 towards mixed purine/pyrimidine sequences of ssDNA and ssRNA in Watson-Crick-type duplexes (Table 4) using the same sequence and conditions as it has been described for INA. Considerable destabilization of TINA/DNA ($\Delta T_m$ in the range of −8.0° C. to −15.5° C.) and TINA/RNA ($\Delta T_m$=−10.0° C.) was observed for 5 as a bulge in the middle of the sequence when compared with the wild-type duplexes. The insertion of the second intercalator 5 as a next-nearest neighbor into DNA (ON24) led to further destabilization of the duplex (ON24/ON25 and ON24/ON27). The incorporation of 5 opposite to each other into two complementary mixed purine-pyrimidine strands, as the complex ON23/ON26, resulted in $T_m$ value of 36.0° C. which was at the same level of magnitude as TINA/DNA duplexes (ON23/ON25 and ON22/ON26). However, when INA was inserted in the same positions in INA/INA duplexes, they were less stable ($T_m$=43.6° C.) than INA/DNA ($T_m$=51.5° C.).

Figure 5:
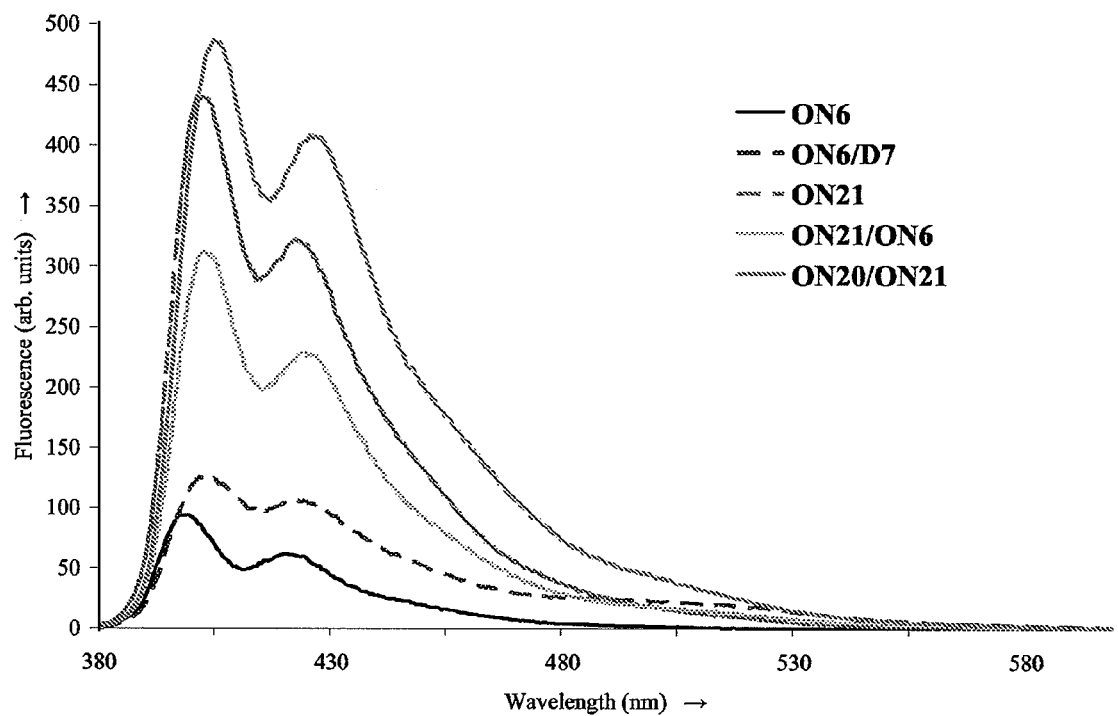
Figure 6:
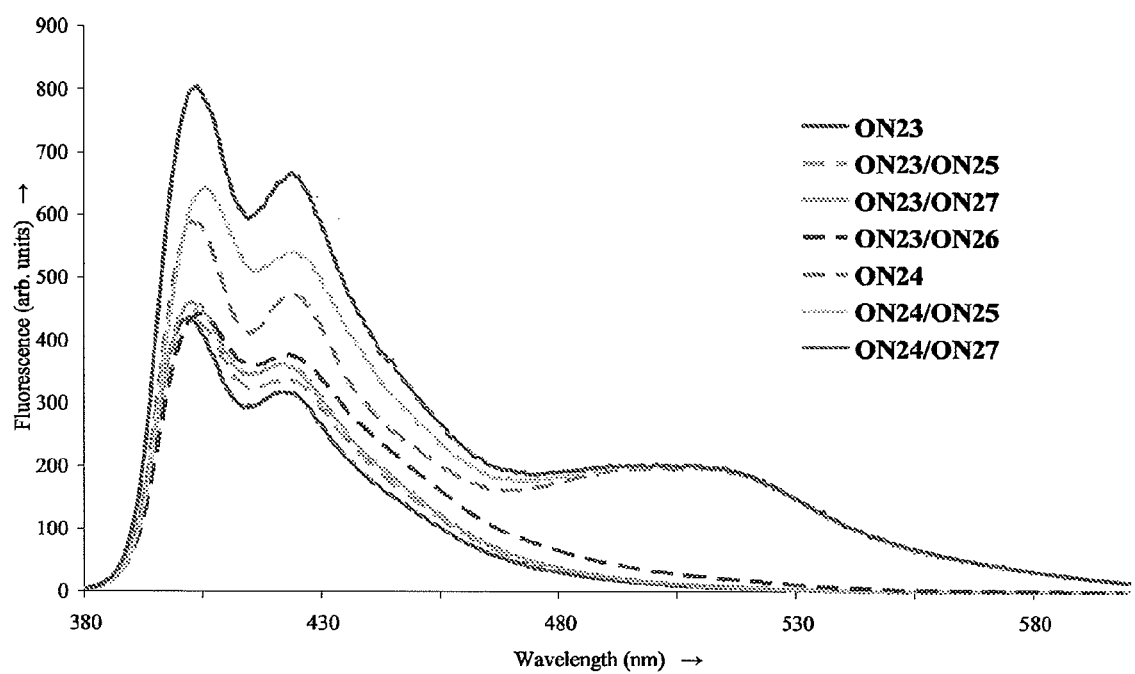

The fluorescence properties of complexes with the 4-(1-pyrenylethynyl)phenyl moiety in the Watson-Crick dsDNA as a duplex alone and as a part of the triplex are shown in FIGS. 4-6. The monomer fluorescence was considerably increased when 5 was inserted into the purine strand (ssON21) compared with the insertion into the pyrimidine strand (ssON6, FIG. 5). A slightly decreased fluorescence intensity was seen upon assembling of the triplexes and duplexes with unmodified DNA and ssON21 (data not shown). It was a surprising finding that the strong sensitivity of the monomer fluorescence of 4-(1-pyrenylethynyl)phenyl moieties in homopyrimidine sequences upon the formation of antiparallel duplexes completely disappeared for mixed sequences (ON23/ON25, ON23/ON27 FIG. 6). This differs also from previous results reported for bulged insertions of (R)-1-O-(1-pyrenylmethyl)glycerol using the same sequences.

When two pyrenyl intercalators 5 were separated by one base-pair, an excimer band observed for the ssON24 (FIG. 6), did not disappear upon formation of the antiparallel duplex (ON24/ON25 and ON24/ON27 FIG. 6). This observation is opposite to the above observations for parallel triplex and parallel duplex with TNA and is also contrary to the previously obtained results for INA.[9b] The presence of the excimer band upon formation of the antiparallel duplex in both homopyrimidine and mixed pyrimidine/purine strands (ON12/ON16 and ON24/ON25, respectively) with bulged 5 as next-nearest neighbors indicates that two pyrenyl residues were positioned very closely and communicated with each other and were not fully embedded into stacking interactions with neighboring Watson-Crick base-pairs. This can also explain the decrease of the antiparallel duplex stability upon incorporation of 5 as a bulge.

We then checked whether an excimer bond could be formed for duplexes and triplexes if two or three dyes were placed opposite to each other, in each of their complementary strand. No excimer band was observed in either parallel duplex ON21/ON6 (FIG. 5) or antiparallel duplexes ON20/ON21 (FIG. 5) and ON23/ON26 (FIG. 6). This result correlates with the work showing that when 4-[4-(1-pyrenylethynyl)phenyl]-1,3-butanediol was positioned opposite each another in the complementary strands of antiparallel dsDNA with mixed sequences. Only for the triplex with three 4-(1-pyrenylethynyl)phenyl moieties placed opposite to each other in all three strands, a weak excimer band at 500 nm was detected (ON6/D7, FIG. 5). The conclusion is that the communication of the 4-(1-pyrenylethynyl)phenyl moieties positioned in different strands of the parallel and antiparallel duplexes and parallel triplex is impeded, which makes zipping of intercalators together with excimer formation unlikely contrary to what was found for INA. Thus, zipping of two pyrene moieties of INA situated opposite to each other in a duplex have been observed in an NMR structure, and this duplex structure led to formation of an excimer band at 480 nm in a steady-state fluorescence spectra upon excitation at 343 nm (unpublished data).

The differences in fluorescence spectra and hybridization properties of the two different pyrene intercalating nucleic acids INA and TINA in Watson-Crick-type duplexes clearly illustrate the consequence of adding an extra 1-phenylethynyl moiety to the aromatic part of (R)-1-O-(1-pyrenylmethyl) glycerol (INA). By this work we have also shown that the common meaning of the poor affinity of pyrene to triplexes is not a general feature because we have succeeded to place pyrene appropriately in the Hoogsteen-type triplex. The ability of intercalators to stabilize parallel triplex structures with only little influence on the stability of dsDNA is known. Thus addition of 2-(2-naphthyl)quinolin-4-amine and analogues thereof lead to considerable stabilization of triplex DNA [$\Delta T_m$=35.6° C. for 2-(2-naphthyl)quinolin-4-amine] with only a little increased hybridization affinity of duplex DNA ($\Delta T_m$=5.5° C.). Similar work reported the synthesis and hybridization properties of oligodeoxynucleotides with perylene coupled either directly or via a propyl linker to the anomeric position of a 2'-deoxyribose residue. One of the advantages of TINA with polycyclic moieties over monomeric triplex-specific intercalators is that TINA can be inserted several times into desired positions of the sequence instead of using excess of the intercalator in the solution. Moreover, high parallel triplex and duplex stabilization together with destabilization of antiparallel duplexes as described here for TINA have never been observed hitherto for other intercalating systems covalently attached to the oligodeoxynucleotides. In this context TINA when incorporated as multiple bulge insertions into oligodeoxynucleotides, it is a unique molecule with the ability to discriminate dsDNA over ssDNA. This feature is clearly seen for ON13 and ON14 when their triplex and antiparallel duplex stabilities are compared at pH 6.0 and pH 5.0 (Table 1). This opens up the possibility of reducing the number of false positives coming from duplex formation when parallel triplex formation is to be detected. This could for example be the case for fluorescence in situ hybridization (FISH) on genomes under non-denaturing conditions and for the purification of plasmid DNA using triple-helix affinity chromatography or triple-helix affinity precipitation which can be performed at pH 6.0 or pH 5.0. This type of discrimination of parallel triplex formation over duplex formation can not be achieved with triplex forming oligos like PNA, LNA or N3'->P5' phosphoramidates which are also known to stabilize antiparallel duplexes.

Using the Sonogoshira-type post-synthetic modification of oligonucleotides possessing (R)-1-O-(4-iodophenyl)methylglycerol we screened several twisted intercalating nucleic acids (TINA) for their ability to increase the thermal stability of Hoogsteen-paired duplexes and triplexes. The insertion of (R)-1-O-[4-(1-pyrenylethynyl)phenylmethyl]glycerol (5) as a bulge in oligodeoxynucleotides was found to be the most effective TINA with good discriminating properties between matched and mis-matched sequences. The Watson-Crick-type DNA/DNA and DNA/RNA duplexes were destabilized upon insertion of TINA in the middle of the sequence compared with native duplexes. We believe that TINA is the first intercalating system covalently attached to oligodeoxynucleotides as a bulge showing increased affinity towards Hoogsteen-type base-pairing and decreased affinity towards Watson-Crick-type helixes. The short synthetic route to the phosphoramidate 8 and post-synthetic Sonogashira modification of oligonucleotides are competitive advantages of TINA over other triplex-stabilizing nucleic acids. From studying double insertions of TINA (5) in one strand it could be concluded that placing of three nucleobases between two bulged (R)-1-O-[4-(1-pyrenylethynyl)phenylmethyl]glycerols may be an optimum for high thermal stability of Hoogsteen DNA helixes. On the other hand the different luminescence properties (excimer band formation) upon insertion of 5 as next-nearest bulged neighbors in the pyrimidine DNA sequence could be used for detection of formation of parallel triplex, parallel dsDNA and antiparallel dsDNA. Increasing the thermal stability in the range of 12-19° C. for TINA with single bulged insertion of 5 can be applied to reduce the required length of the TFO. Moreover, good thermal stability for Hoogsteen-type duplexes and triplexes could be obtained at pH 7.0 even in the presence of several cytosines in the sequence (up to 36% in the present work). The multiple insertions of 5 can be used to increase the melting temperature of less stable Hoogsteen duplexes to the level of Watson-Crick duplexes of the same length under proper conditions (sequence, pH, salt concentration etc). Considering the development of modified nucleic bases with high affinity for C-G and T-A inversion sites in dsDNA along with alternate-stranded triplexes, we think such improvements of triplex formation will expand the applicability of TINA. The ability to stabilize the triplex upon insertion of 5 into the pyrimidine strands of circular oligodeoxynucleotides or clamps to target ssDNA and ssRNA is also an obvious possibility. As a next step, studies are devoted to the influence of insertion of TINA and INA on the stability of nucleic acid helixes different from the classical Watson-Crick and Hoogsteen complexes. Thus there is still limited availability of nucleic acid analogues which can stabilize reverse-Hoogsteen base-pairing, i-motifs (C-C$^+$ base-pairs) or quadruplexes (G-rich sequences). We believe that the ability of TINA to stabilize parallel triplexes and duplexes along with discrimination of Hoogsteen over Watson-Crick type nucleic acid helixes can make TINA very useful in the design of DNA-based tools in bio- and nano-technology where specific recognition, high thermal stability and self-organization or reorganization are vital.

TABLE 1

T$_m$ [° C.] data for triplex and duplex melting, taken from UV-melting curves (λ = 260 nm).

| SEQ ID NO. | No. | Sequence | Triplex[a] 3'-CTGCCCCTTTCTTTTTT (SEQ ID NO. 29) 5'-GACGGGGAAAGAAAAAA (SEQ ID NO. 28) (D1) | | | Parallel duplex[b] 5'-GACGGGGAAAGAAAAAA (ON15) (SEQ ID NO. 15) | | Antiparallel duplex[c] 3'-GGGGAAAGAAAAAA (ON16) (SEQ ID NO. 16) | | |
|---|---|---|---|---|---|---|---|---|---|---|
| | | | pH 5.0 | pH 6.0 | pH 7.2 | pH 5.0 | pH 6.0 | pH 5.0 | pH 6.0 | pH 7.2 |
| SEQ ID NO. 1 | ON1 | 5'-CCCCTTTCTTTTTT | 55.0[e] | 27.0 | <5.0 | 29.5 | 19 | 47.0 | 48.0 | 47.0 |
| SEQ ID NO. 2 | ON2 | 5'-CCCCTT1TCTTTTTT | —[l] | 15.0 | <5.0 | —[l] | <5.0 | —[l] | 40.5 | —[l] |
| SEQ ID NO. 3 | ON3[f] | 5'-CCCCT2TCTTTTTT | —[l] | 26.0 | <5.0 | —[l] | <5.0 | —[l] | 42.0 | —[l] |
| SEQ ID NO. 4 | ON4[g] | 5'-CCCCT3TCTTTTTT | —[l] | 26.0 | <5.0 | —[l] | 17.0 | —[l] | 40.0 | —[l] |
| SEQ ID NO. 5 | ON5[f] | 5'-CCCCT4TCTTTTTT | 57.0 | 35.0 | 13.5 | 33.5 | 22.0 | 44.5 | 45.0 | 46.0 |
| SEQ ID NO. 6 | ON6[f,g] | 5'-CCCCT5TCTTTTTT | 59.0[e] | 46.0 | 28.0 | 42.0 | 33.5 | 44.0 | 46.5 | 45.5 |
| SEQ ID NO. 7 | ON7[f] | 5'-CCCCTTTC5TTTTTT | —[l] | 39.5 | 21.5 | —[l] | 30.0 | —[l] | 44.5 | —[l] |
| SEQ ID NO. 8 | ON8[f] | 5'-CCCCTTT5CTTTTTT | —[l] | 42.5 | 26.0 | —[l] | 28.0 | —[l] | 45.0 | —[l] |
| SEQ ID NO. 9 | ON9[g] | 5'-CCC5CTTTCTTTTTT | —[l] | 41.0 | 24.0 | —[l] | 31.5 | —[l] | 45.5 | —[l] |
| SEQ ID NO. 10 | ON10[f] | 5'-5CCCCTTTCTTTTTT | 61.0 | 44.5 | 20.5 | 46.0 | 36.0 | 49.5 | 53.0 | 52.0 |
| SEQ ID NO. 11 | ON11[g] | 5'-5CCCCT5TCTTTTTT | 65.5[e] | 57.0[d] | 35.5 | 53.5 | 45.5 | 46.5 | 47.0 | 46.5 |
| SEQ ID NO. 12 | ON12[k] | 5'-CCCCT5T5CTTTTTT | 55.5[e] | 40.0 | <5.0 | 37.0 | 26.5 | 37.5 | 41.0 | 41.0 |
| SEQ ID NO. 13 | ON13[k] | 5'-CCCCT5T5CTTTTTT | 59.5[e] | 56.5[e] | 40.0 | 41.0 | 38.0 | 44.5 | 45.0 | 42.0 |
| SEQ ID NO. 14 | ON14[k] | 5'-CCCCT5TCT5TTTTT | 63.0[e] | 56.5[e] | 43.0 | 45.5 | 38.0 | 42.5 | 41.0 | 38.0 |

[a] c = 1.5 μM of ON1-14 and 1.0 μM of each strand of dsDNA (D1) in 20 mm sodium cacodylate, 100 mm NaCl, 10 mm MgCl$_2$, pH 6.0 and 7.2; duplex T$_m$ = 56.5 (pH 5.0), 58.5° C. (pH 6.0) and 57.0° C. (pH 7.2);
[b] c = 1.0 μM of each strand in 20 mm sodium cacodylate, 100 mm NaCl, 10 mm MgCl$_2$, pH 6.0 or pH 5.0;
[c] c = 1.0 μM of each strand in 20 mm sodium cacodylate, 100 mm NaCl, 10 mm MgCl$_2$, pH 6.0 or pH 5.0;
[d] Third strand and duplex melting overlaid. Transition state with T$_m$ = 54.5° C. was determined at 373 nm;
[e] Third strand and duplex melting overlaid;
[f] Prepared by Sonogashira reaction mixture: Pd(PPh$_3$)$_2$Cl$_2$ (7.5 mM), corresponding acetylene (22.5 mM), CuI (7.5 mM), dry DMF/Et$_3$N (3.5/1.5, 500 μL), 3 h;
[g] Prepared by Sonogashira reaction mixture: Pd(PPh$_3$)$_4$ (7.5 mM), corresponding acetylene (22.5 mM), CuI (7.5 mM), dry DMF/Et$_3$N (3.5/1.5, 500 μL), 3 h;
[k] Prepared by double treatment with Sonogashira reaction mixture: Pd(PPh$_3$)$_4$ (7.5 mM), 1-ethynylpyrene (22.5 mM), CuI (7.5 mM), dry DMF/Et$_3$N (3.5/1.5, 500 μL), 3 h;
[l] not determined.

TABLE 2

T$_m$ [° C.] data for mis-matched parallel triplex[a] and parallel duplex[b] melting, taken from UV-melting curves (λ = 260 nm), pH 6.0.

| SEQ ID NO | | Sequence 3'-CTGCCCCTTXCTTTTTT (X = T, SEQ ID NO. 29; X = A, SEQ ID NO. 30; X = C, SEQ ID NO 31; X = G, SEQ ID NO. 32) 5'-GACGGGGAAYGAAAAAA (Y = A, SEQ ID NO. 28; Y = T, SEQ ID NO. 17; Y = G, SEQ ID NO. 18; Y = C, SEQ ID NO 19) | D1: X·Y = T·A | D2: X·Y = A·T | D3: X·Y = C·G | D4: X·Y = G·C |
|---|---|---|---|---|---|---|
| SEQ ID NO. 1 | ON1 | 5'-CCCCTTTCTTTTTT | 27.0 | <5.0 | <5.0 | <5.0 |
| SEQ ID NO. 6 | ON6 | 5'-CCCCTT5CTTTTTTT | 46.0 | 27.0 | 34.5 | 28.5 |
| SEQ ID NO. 8 | ON8 | 5'-CCCCTTT5CTTTTTT | 42.5 | 28.5 | 26.5 | 26.5 |
| SEQ ID NO. 10 | ON10 | 5'-5CCCCTTTCTTTTTT | 44.5 | 22.5 | 27.0 | 28.0 |

TABLE 2-continued $T_m$ [° C.] data for mis-matched parallel triplex[a] and parallel duplex[b] melting, taken from UV-melting curves (λ = 260 nm), pH 6.0.

| SEQ ID NO. 11 | ON11 | 5'-5CCCCTT5TCTTTTTT | 57.0 | 40.5 | 45.5 | 42.0 |
|---|---|---|---|---|---|---|
| | | 5'-GACGGGGAAYGAAAAAA (Y = A, SEQ ID NO. 15; Y = T, SEQ ID NO. 17; Y = G, SEQ ID NO. 18; Y = C, SEQ ID NO 19) | ON15 Y = A | ON17 Y = T | ON18 Y = G | ON19 Y = C |
| SEQ ID NO. 1 | ON1 | 5'-CCCCTTTCTTTTTT | 19.0 | <5.0 | 10.0 | <5.0 |
| SEQ ID NO. 6 | ON6 | 5'-CCCCTT5TCTTTTTT | 33.5 | 21.5 | 20.5 | 20.5 |
| SEQ ID NO. 8 | ON8 | 5'-CCCCTTT5CTTTTTT | 28.0 | 20.0 | 18.5 | 20.0 |

[a] C = 1.5 µM of ON1-14 and 1.0 µM of each strand of dsDNA in 20 mM sodium cacodylate, 100 mM NaCl, 10 mM MgCl$_2$, pH 6.0;
[b] C = 1.0 µM of ON1-14 and 1.0 µM of purine strand.

TABLE 3

$T_m$ [° C.] data for parallel triplex meltings[a] for insertions of 5 in the sequence of the Watson-Crick duplex, taken from UV-melting curves (λ = 260 nm), pH 6.0. The meltings are also given for parallel duplexes[b] with insertion of 5 in the purine stretch,

| | | | Triplex | | | | Parallel duplex | |
|---|---|---|---|---|---|---|---|---|
| SEQ ID NO. | | Sequence | D1 | D5: 3'CTGCCCCTT5TCTTTTTT (SEQ ID NO. 20) (ON20)[c] 5'-GACGGGGAAAGAAAAAA | D6: 3'-CTGCCCCTTTCTTTTTT (SEQ ID NO. 29) 5'-GACGGGGAA5AGAAAAAA (SEQ ID NO. 21) (ON21)[d] | D7: ON20/ ON21 | ON15 | ON21 |
| SEQ ID NO. 1 | ON1 | 5'-CCCCTTTCTTTTTT | 27.0 | 38.0 | 24.0 | 27.0 | 19.0 | 14.0 |
| SEQ ID NO. 6 | ON6 | 5'-CCCCTT5TCTTTTTT | 46.0 | 38.0 | 27.5 | 31.5 | 33.5 | 26.5 |
| SEQ ID NO. 9 | ON9 | 5'-CCC5CTTTCTTTTTT | 41.0 | 52.5[d] | 41.5 | 43.5 | 31.5 | 29.0 |

[a] C = 1.5 µM of ON1, ON6, ON9 and 1.0 µM of each strand of dsDNA in 20 mM sodium cacodylate, 100 mM NaCl, 10 mM MgCl$_2$, pH 6.0, duplex $T_m$ = 55.0° C. (D5), 56.0° C. (D6), 57.0° C. (D7);
[b] C = 1.0 µM of ON1, ON6, ON9, ON15 and ON21 in 20 mM sodium cacodylate, 100 mM NaCl, 10 mM MgCl$_2$, pH 6.0;
[c] Prepared by Sonogashira reaction mixture: Pd(PPh$_3$)$_4$ (7.5 mM), 1-ethynylpyrene (22.5 mM), CuI (7.5 mM), dry DMF/Et$_3$N (3.5/1.5, 500 µL), 3h;
[d] Prepared by double treatment with Sonogashira reaction mixture: Pd(PPh$_3$)$_4$ (7.5 mM), 1-ethynylpyrene (22.5 mM), CuI (7.5 mM), dry DMF/Et$_3$N (3.5/1.5, 500 µL), 3h;
[d] Third strand and duplex melting overlaid.

TABLE 4

$T_m$ [° C.] data for antiparallel duplex[a] melting, taken from UV-melting curves (λ = 260 nm).

| | No | | ON25 DNA 5'-AGCTTGCTTGAG (SEQ ID NO. 25) | ON26[b] DNA 5'-AGCTTG5CTTGAG (SEQ ID NO. 26) | ON27 RNA 5'-AGCUUGCUUGAG (SEQ ID NO. 27) |
|---|---|---|---|---|---|
| SEQ ID NO. 22 | ON22 | 3'-TCGAACGAACTC | 47.5 | 32.0 | 40.5 |
| SEQ ID NO. 23 | ON23[b] | 3'-TCGAAC5GAACTC | 39.5 | 36.0 | 30.5 |
| SEQ ID NO. 24 | ON24[c] | 3'-TCGAAC5G5AACTC | 34.0 | 22.5 | 25.0 |

[a] C = 1.0 µM of each oligonucleotide in 140 mM NaCl, 10 mM sodium phosphate buffer, 1 mM EDTA, pH 7.0;
[b] Sonogashira reaction mixture: Pd(PPh$_3$)$_4$ (7.5 mM), 1-ethynylpyrene (22.5 mM), CuI (7.5 mM), dry DMF/Et$_3$N (3.5/1.5, 500 µL), 3h;
[c] Double treatment with Sonogashira reaction mixture: Pd(PPh$_3$)$_4$ (7.5 mM), 1-ethynylpyrene (22.5 mM), CuI (7.5 mM), dry DMF/Et$_3$N (3.5/1.5, 500 µL), 3h.

NMR spectra were recorded on a Varian Gemini 2000 spectrometer at 300 MHz for $^1$H and 75 MHz for $^{13}$C Internal standards used in $^1$H NMR spectra were TMS (δ: 0.00) for CDCl$_3$; in $^{13}$C NMR were CDCl$_3$ (δ: 77.0). Accurate ion mass determinations were performed using the 4.7 Tesla Ultima Fourier transform (FT) mass spectrometer (Ion Spec, Irvine, Calif.). The [M+Na]$^+$ ions were peak matched using ions derived from the 2,5-dihydroxybenzoic acid matrix. Thin layer chromatography (TLC) analyses were carried out with use of TLC plates 60 F$_{254}$ purchased from Merck and were visualized in an UV light (254 nm). The silica gel (0.040-0.063 mm) used for column chromatography was purchased from Merck. Solvents used for column chromatography were distilled prior to use, while reagents were used as purchased.

Example 2

Preparation of (S)-1-(4,4'-dimethoxytriphenylmethyloxy)-3-(4-iodobenzyloxy)propan-2-ol. (S)-(+)-2,2-Dimethyl-1,3-dioxolane-4-methanol (6, 1.17 g, 8.9 mmol) and 4-iodobenzylbromide (2.5 g, 8.4 mmol) were refluxed under Dean-Stark conditions in toluene (80 mL) in the presence of KOH (8.8 g, 154.0 mmol) for 12 h. The reaction mixture was allowed to cool down and H$_2$O (30 mL) was added. After separation of the phases the water layer was washed with toluene (2×15 mL). Combined organic layers were washed with H$_2$O (30 mL) and concentrated in vacuo. The residue was treated with 80% aq. AcOH (25 mL) for 48 h at rt. The solvent was removed in vacuo and the residue was co-evaporated twice with toluene/EtOH (30 mL, 5:1, v/v). The residue was dried under diminished pressure to afford (R)-3-(4-iodobenzyloxy)propane-1,2-diol (7, 100%, 2.3 g) as yellowish oil that was used in the next step without further purification.

This oil (2.3 g, 8.4 mmol) was dissolved in anh. pyridine (25 mL) and 4,4'-dimethoxytrityl chloride (3.5 g, 10.4 mmol) was added under nitrogen. After 24 h MeOH (2 mL) followed by EtOAc (150 mL) were added and the mixture was extracted with std. aq. NaHCO$_3$ (40 mL×2). The water phase was extracted with EtOAc (20 mL×2). The combined organic layers were dried (Na$_2$SO$_4$), filtered and evaporated under diminished pressure. The residue was co-evaporated twice with toluene/EtOH (25 mL, 1:1, v/v). The residue was adsorbed on a silica gel (1.5 g) from EtOAc (30 mL) and purified using dry column vacuum chromatography with EtOAc (0-30%, v/v) in petroleum ether to afford compound (S)-1-(4,4'-dimethoxytriphenylmethyloxy)-3-(4-iodobenzyloxy)propan-2-ol (70%, 3.6 g) as a yellow foam. $^1$H NMR (CDCl$_3$) δ 2.42 (br.s., 1H, OH), 3.20 (m, 2H, CH(OH)CH$_2$OCH$_2$), 3.56 (m, 2H, CH$_2$ODMT), 3.78 (s, 6H, 2×OCH$_3$), 3.97 (m, 1H, CHOH), 4.43 (s, 2H, CH$_2$Ar), 6.78 (d, 4H, J=8.5 Hz, DMT), 7.00 (d, 2H, J=8.0 Hz, iodophenyl), 7.30-7.45 (m, 9H, DMT), 7.63 (d, 2H, J=8.0 Hz, iodophenyl); $^{13}$C NMR (CDCl$_3$) δ 5.2 (OCH$_3$), 62.2 (CH$_2$ODMT), 69.9 (CH(OH)CH$_2$OCH$_2$), 71.6 (CHOH), 72.6 (CH$_2$-iodophenyl), 86.1 [C(Ar)$_3$], 93.1, 129.4, 137.4, 137.7 (iodophenyl), 113.1, 126.7, 127.8, 128.1, 130.0, 135.9, 144.7, 158.5 (DMT). HR-MALDI-MS calcd for C$_{31}$H$_{31}$IO$_5$Na [M+Na]$^+$ m/z 633.1108, found m/z 633.1116.

Example 3

Preparation of (S)-2-O-[2-cyanoethoxy(diisopropylamino)phosphino]-1-O-(4,4'-dimethoxytriphenylmethyl)-3-O-(4-iodobenzyl)glycerol (compound 8 in scheme 2). (S)-1-(4,4'-Dimethoxytriphenylmethyloxy)-3-(4-iodobenzyloxy)propan-2-ol (2.0 g, 3.3 mmol) was dissolved under nitrogen in anh. CH$_2$Cl$_2$ (50 mL). N,N-Diisopropylammonium tetrazolide (0.850 g, 5.0 mmol) was added followed by dropwise addition of 2-cyanoethyl tetraisopropylphosphordiamidite (1.1 g, 3.7 mmol) under external cooling with ice-water bath. After 16 h analytical TLC showed no more starting material and the reaction was quenched with H$_2$O (30 mL). Layers were separated and the organic phase was washed with H$_2$O (30 mL). Combined water layers were washed with CH$_2$Cl$_2$ (25 mL). The org. phase was dried (Na$_2$SO$_4$), filtered, silica gel (1.5 g) and pyridine (0.5 mL) were added and solvents were removed under reduced pressure. The residue was purified using silica gel dry column vacuum chromatography with NEt$_3$ (0.5%, v/v)/EtOAc(0-25%,)/petroleum ether. Combined UV-active fractions were evaporated in vacuo affording the final compound 8 (1.8 g, 67%) as a foam that was used in ODN synthesis. $^{32}$P NMR (CDCl$_3$) δ 149.8, 149.9 in ratio 1:1. HR-ESI-MS calcd for C$_{40}$H$_{46}$IO$_6$N$_2$PLi [M+Li]$^+$ m/z 817.2449, found m/z 817.2447.

Example 4

Preparation of (R)-1-O-(4,4'-dimethoxytriphenylmethyl)-3-O-[4-(1-pyrenylethynyl)phenylmethyl]glycerol. To the solution of (R)-3-(4-iodobenzyloxy)propane-1,2-diol (4.2 mmol) in DMF (40 mL), Et$_3$N (5.8 mL) was added and Ar was bubbled through the solution 30 min. Afterwards, 1-ethynylpyrene (1.05 g, 4.65 mmol) was dissolved under Ar and CuI (56 mg, 0.3 mmol) and Pd(PPh$_3$)$_4$ (125 mg, 0.11 mmol) were added to the solution. Reaction mixture was stirred at rt under Ar overnight, followed by adding of CH$_2$Cl$_2$ (150 mL) and extraction with 0.3 M aq. solution of ammonium salt of EDTA (2×75 mL). Organic layer was washed with H$_2$O (3×75 mL), dried (Na$_2$SO$_4$), filtered and evaporated in vacuo to dryness. The residue was co-evaporated twice with toluene/EtOH (30 mL, 1:1, v/v) affording 1-O-[4-(1-pyrenylethynyl)phenylmethyl]glycerol as an oil (3.1 g). The oil was co-evaporated with pyridine (20 mL) and then dissolved in anh. pyridine (50 mL), cooled by ice-water bath and 4,4'-dimethoxytrityl chloride (1.45 g, 4.41 mmol) was added under Ar. Reaction mixture was stirred at rt for 16 h and then extra portion of 4,4'-dimethoxytrityl chloride (0.5 g, 1.5 mmol) was added. After 24 h TLC showed no more starting material and reaction mixture was quenched by MeOH (2 mL) and diluted by EtOAc (150 mL) and extracted with std. aq. NaHCO$_3$ (100 mL×2). The water phase was extracted with EtOAc (50 mL×2). The combined organic layers were dried (Na$_2$SO$_4$), filtered and evaporated under diminished pressure. The residue was co-evaporated twice with toluene/EtOH (25 mL, 1:1, v/v). The residue was adsorbed on a silica gel (2.0 g) from EtOAc (50 mL) and purified using dry column vacuum chromatography with EtOAc (0-100%, v/v) in cyclohexane to afford (S)-1-O-(4,4'-dimethoxytriphenylmethyl)-3-O-[4-(1-pyrenylethynyl)phenylmethyl]glycerol. (60%, 1.75 g) as a yellow foam. $^1$H NMR (CDCl$_3$) δ 2.48 (d, 1H, J=5.0 Hz, OH), 3.24 (m, 2H, CH(OH)CH$_2$OCH$_2$), 3.31 (m, 2H, CH$_2$ODMT), 3.78 (s, 6H, 2×OCH$_3$), 4.00 (m, 1H, CHOH), 4.58 (s, 2H, CH$_2$Ar), 6.80 (d, 4H, J=8.5 Hz, DMT), 7.10-7.45 (m, 11H, DMT), 7.72 (d, 2H, J=8.0 Hz, phenyl), 8.00-8.30 (m, 9H, pyren-1-yl); $^{13}$C NMR (CDCl$_3$) δ 5.2 (OCH$_3$), 64.3 (CH$_2$ODMT), 70.0 (CH(OH)CH$_2$OCH$_2$), 71.7 (CHOH), 72.9 (CH$_2$-phenyl), 86.1 [C(Ar)$_3$], 88.7, 94.9 (C≡C), 117.7, 127.7, 138.5, 139.4 (phenyl), 113.1, 124.5-131.8, 136.0, 144.8, 158.5 (DMT, pyren1-yl). HR-MALDI-MS: m/z calcd for C$_{49}$H$_{40}$Na$^+$O$_5$ [M+Na]$^+$ 731.2768, found 731.2739.

Example 5

Preparation of (R)-2-O-[2-cyanoethoxy(diisopropylamino)phosphino]-1-O-(4,4'-dimethoxytriphenylmethyl)-3-O-[4-(1-pyrenylethynyl)phenylmethyl]glycerol.

The compound was prepared using the same procedure as for compound 8 using (R)-1-O-(4,4'-dimethoxytriphenylmethyl)-3-O-[4-(1-pyrenylethynyl)phenylmethyl]glycerol (1.7 g, 2.4 mmol), N,N-diisopropylammonium tetrazolide (0.620 g, 3.6 mmol), 2-cyanoethyl tetraisopropylphosphordiamidite (1.150 g, 3.8 mmol), anh. $CH_2Cl_2$ (50 mL) for 24 h. The final compound was obtained (1.8 g, 83%) as a foam that was used in ODN synthesis. $^{32}P$ NMR ($CDCl_3$) δ 150.3, 150.5 in a ratio 3:2. HR-MALDI-MS: m/z calcd for $C_{58}H_{57}N_2Na^+O_6P$ [M+Na]$^+$ 931.3846, found 931.3814.

Example 6

Synthesis and Purification of TINAs Using Post-Synthetic Approach

ODNs were synthesized on an Expedite™ Nucleic Acid Synthesis System Model 8909 from Applied Biosystems using 4,5-dicyanoimidazole as an activator and an increased deprotection time (100 sec) and coupling time (2 min) for 0.075 M solution of the phosphoramidite 8 in a 1:1 mixture of dry $MeCN/CH_2Cl_2$. After the DNA synthesis, the columns with CPG-supports and DMT-on oligonucleotides possessing 4-iodophenyl moieties were flushed with argon (2 min) prior to the coupling reaction. Sonogashira-coupling reagent mixture containing $Pd(PPh_3)_4$ or $Pd(PPh_3)_2Cl_2$ (7.5 mM), an aromatic structure possessing a terminal acetylene (22.5 mM), and CuI (7.5 mM) in dry $DMF/Et_3N$ (3.5/1.5, 500 µL) was prepared in 1 mL plastic syringe under dry conditions at room temperature. Syringes were also flushed with argon prior to use. The syringe with Sonogashira-coupling reagent mixture was attached to the column with the CPG and another empty syringe was connected from another side of the column. The CPG-support with modified oligonucleotide was washed with the reaction mixture several times by syringes. After every 45 min the last operation was repeated. After 3-4 h the reaction mixture was removed from the support and columns were washed with DMF (2×0.5 mL) and $CH_3CN$ (2×1 mL), and dried. In cases of ON12-ON14, ON21 and ON24, CPG-supports were treated one more time with freshly prepared Sonogashira-coupling reaction mixture. Afterwards the 5'-DMT-on oligonucleotides were cleaved off from the solid support (room temperature, 2 h) and deprotected (55° C., overnight) using 32% aqueous ammonia. Purification of 5'-O-DMT-on TINAs was accomplished using a reverse-phase semi-preparative HPLC on Waters Xterra™ MS $C_{18}$ column. The ODNs were DMT deprotected in 100 µL 10% aq. acetic acid (30 min), diluted with 32% aqueous ammonia (1 mL) and purified again on HPLC. Corresponding fractions with ODNs were evaporated, diluted with 1M aq. NaOAc (150 µL), and ODNs were precipitated from ethanol (550 µL). The modified ODNs were confirmed by MALDI-TOF analysis on a Voyager Elite Biospectrometry Research Station from PerSeptive Biosystems. The purity of the final TFOs was checked by ion-exchange chromatography using LaChrom system from Merck Hitachi on GenPak-Fax column (Waters).

Example 7

Synthesis and purification of TINAs using (R)-2-O-[2-cyanoethoxy(diisopropylamino)phosphino]-1-O-(4,4'-dimethoxytriphenylmethyl)-3-O-[4-(1-pyrenylethynyl)phenylmethyl]glycerol.

ODNs were synthesized on an Expedite™ Nucleic Acid Synthesis System Model 8909 from Applied Biosystems using 4,5-dicyanoimidazole as an activator and an increased deprotection time (100 sec) and coupling time (2.5 min) for 0.075 M solution of the said phosphoramidite in a 1:1 mixture of dry $MeCN/CH_2Cl_2$. After the completed DNA synthesis the 5'-DMT-on oligonucleotides were cleaved off from the solid support (rt, 2 h) and deprotected (55° C., overnight) using 32% aqueous ammonia. Purification of 5'-O-DMT-on TINAs was accomplished using a reverse-phase semi-preparative HPLC on Waters Xterra™ MS $C_{18}$ column. The ODNs were DMT deprotected in 100 µL 80% aq. acetic acid (30 min), diluted with 1M aq. NaOAc (150 µL) and precipitated from ethanol (550 µL). The modified ODNs were confirmed by MALDI-TOF analysis on a Voyager Elite Biospectrometry Research Station from PerSeptive Biosystems. The purity of the final TFOs was checked by ion-exchange chromatography using LaChrom system from Merck Hitachi on GenPak-Fax column (Waters).

Example 8

Melting Temperature Measurements

Melting temperature measurements were performed on a Perkin-Elmer UV/VIS spectrometer Lambda 35 fitted with a PTP-6 temperature programmer. The triplexes were formed by first mixing the two strands of the Watson-Crick duplex, each at a concentration of 1.0 µM in the corresponding buffer solution. The solution was heated to 80° C. for 5 min, cooled to rt and the third (TFO) strand was added and then kept at 15° C. for 30 min. The duplexes were formed by mixing the two strands, each at a concentration of 1.0 µM in the corresponding buffer solution followed by heating to 70° C. for 5 min and then cooling to rt. The melting temperature ($T_m$, ° C.) was determined as the maximum of the first derivative plots of the melting curves obtained by measuring absorbance at 260 nm against increasing temperature (1.0° C. per 1 min). Lower speed of increasing the temperature (0.5° C. per 1 min) resulted in the same curves. Experiments were also done at 373 nm. All melting temperatures are within the uncertainty ±1.0° C. as determined by repetitive experiments.

Example 9

Fluorescence Measurements

Fluorescence measurements were performed on a Perkin-Elmer luminescence spectrometer LS-55 fitted with a Julabo F25 temperature controller. The triplexes and duplexes were formed in the same way as for $T_m$ measurements except that only 1.0 µM of TFOs were used in all cases. The spectra were recorded at 10° C. in the buffer 20 mM sodium cacodylate, 100 mM NaCl, 10 mM $MgCl_2$ at pH 6.0.

Example 10

MALDI-TOF MS, Reverse-Phase (DMT-on) and Ion-Exchange (DMT-off) HPLC Analysis of Oligonucleotides Synthesized

| Oligonucleotides | m/z $[M + H]^+$, calcd (Da) | m/z $[M + H]^+$, found (Da) | RP-HPLC, $R_t$ (min)[a] | IE-HPLC, purity[d] |
|---|---|---|---|---|
| ON2 | 4490.8 | 4489.2 | 15.1 | 90% |
| ON3 | 4489.1 | 4488.9 | 15.2/38.1[b] | 90% |
| ON4 | 4541.1 | 4541.6 | 16.2 | 95% |
| ON5 | 4516.0 | 4518.2 | 15.8 | 95% |
| ON6 | 4589.2 | 4589.2 | 16.0 | 96% |
| ON7 | 4589.2 | 4593.0 | 16.1 | 93% |
| ON8 | 4589.2 | 4588.2 | 16.1 | 95% |
| ON9 | 4589.2 | 4588.2 | 16.3 | 97% |
| ON10 | 4589.2 | 4589.2 | 18.7 | 91% |
| ON11 | 5054.6 | 5058.9 | 18.6 | 94% |
| ON12 | 5054.6 | 5060.1 | 17.4/32.9[c] | 93% |
| ON13 | 5054.6 | 5058.0 | 17.1 | 97% |
| ON14 | 5054.6 | 5058.2 | 17.0 | 93% |
| ON20 | 5510.8 | 5513.1 | 16.2 | 95% |
| ON21 | 5802.4 | 5799.7 | 27.2[c] | 86% |
| ON23 | 4081.8 | 4083.1 | 16.2 | 88% |
| ON24 | 4549.3 | 4551.2 | 17.4 | 91% |
| ON26 | 4143.8 | 4143.9 | 15.8 | 85% |

[a]Waters Delta Prep 4000 Preparative Chromatography System. Buffer A [950 mL of 0.1 M $NH_4HCO_3$ and 50 mL of $CH_3CN$, (pH = 9.0)] and buffer B [250 mL of 0.1 $NH_4HCO_3$ and 750 mL of $CH_3CN$, (pH = 9.0)]. Flow 2.5 mL/min. Gradients: 4 min 100% A, linear gradient to 100% B in 11 min, 100% B in 5 min, then linear gradient to 100% A in 2 min and 100% A in 3 min;
[b]Waters Delta Prep 4000 Preparative Chromatography System, the same buffer as in[a]. Flow 1.0 mL/min. Gradients: 5 min 100% A, linear gradient to 70% B in 30 min, 2 min with 70% B, linear gradient to 100% B in 8 min and then 100% A in 15 min;
[c]Waters Delta Prep 700 Semi-preparative Chromatography System. Buffer A [0.05 M triethyl ammonium acetate in $H_2O$ (pH = 7.0)] and buffer B (75% $CH_3CN$ in $H_2O$). Flow 2.5 mL/min. Gradients: 2 min 100% A, linear gradient to 70% B in 38 min, linear gradient to 100% B in 7 min, 100% B in 3 min and then 100% A in 10 min;
[d]LaChrom system from Merck Hitachi on GenPak-Fax column (Waters). Buffer A [25 mM Tris-HCl, 10 mM EDTA in $H_2O$ (pH = 8.0)] and buffer B (1 M NaCl in $H_2O$). Flow 0.75 mL/min. Gradients: 5 min 97% A and 3% B, linear gradient to 35% B in 41 min, linear gradient to 75% B in 3 min and then 10 min 97% A and 3% B.

The invention claimed is:

1. An oligonucleotide comprising a flexible basestacking monomer with the structure $$X-L-I_1-C-I_2$$

wherein:

X is a backbone monomer unit that can be incorporated into the backbone of a oligonucleotide or a oligonucleotide analogue, or PNA, or PNA analogues, wherein X comprises an alkylenediol, ethyleneglycol, or 1-O-methyleneglycerol, which optionally has the alkylenediol partly comprised in a ring system, L is a linker, $I_1$ is a first intercalator comprising at least one essentially flat conjugated system, which is capable of co-stacking with nucleobases of DNA, RNA or analogues thereof, wherein $I_1$ is a monocyclic or polycyclic aromatic ring system selected from benzene, naphthalene, azulene, or bicyclic heteroaromatic ring systems or substitutions thereof, C is a conjugator selected from alkyl of 1 to 12 carbons, alkenyl of 2 to 12 carbons, alkynyl of 2 to 25 carbons or diazo or combinations thereof with a length of no more than 25 carbon or nitrogen atoms, and $I_2$ is a second intercalator comprising at least one essentially flat conjugated system, which is capable of co-stacking with nucleobases of DNA, RNA or analogues thereof, wherein $I_2$ is selected from bi-cyclic aromatic ring systems, tricyclic aromatic ring systems, tetracyclic aromatic ring systems, pentacyclic aromatic ring systems or heteroaromatic analogues thereof or substitutions thereof, and wherein the flexible basestacking monomer leads to high thermal stability of Hoogsteen-type triplexes and duplexes, and wherein the oligonucleotide comprising a flexible basestacking monomer comprises the structure

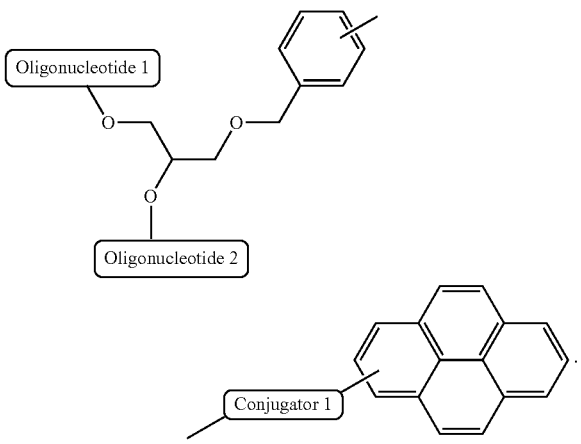

2. The oligonucleotide of claim 1 wherein the phenyl ring is ortho-substituted.

* * * * *